(12) United States Patent
Lichenstein et al.

(10) Patent No.: US 10,350,213 B2
(45) Date of Patent: *Jul. 16, 2019

(54) METHODS FOR TREATING CANCER USING APILIMOD

(71) Applicant: AI Therapeutics, Inc., Guilford, CT (US)

(72) Inventors: Henri Lichenstein, Guilford, CT (US); Jonathan M. Rothberg, Guilford, CT (US); Sophia Gayle, East Haven, CT (US); Neil Beeharry, Guilford, CT (US); Paul Beckett, Yorktown Heights, NY (US); Sean Landrette, Meriden, CT (US); Chris Conrad, Guilford, CT (US); Tian Xu, Guilford, CT (US)

(73) Assignee: AI Therapeutics, Inc., Guilford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/213,829

(22) Filed: Jul. 19, 2016

(65) Prior Publication Data

US 2017/0020884 A1 Jan. 26, 2017

Related U.S. Application Data

(60) Provisional application No. 62/194,367, filed on Jul. 20, 2015.

(51) Int. Cl.
| | | |
|---|---|---|
| *A61K 31/5377* | (2006.01) | |
| *A61K 31/506* | (2006.01) | |
| *A61K 45/06* | (2006.01) | |
| *A61K 31/454* | (2006.01) | |
| *A61K 31/4745* | (2006.01) | |
| *A61K 31/519* | (2006.01) | |
| *A61K 31/573* | (2006.01) | |
| *A61K 31/664* | (2006.01) | |
| *A61K 31/704* | (2006.01) | |
| *A61K 31/44* | (2006.01) | |

(52) U.S. Cl.
CPC .......... *A61K 31/5377* (2013.01); *A61K 31/44* (2013.01); *A61K 31/454* (2013.01); *A61K 31/4745* (2013.01); *A61K 31/506* (2013.01); *A61K 31/519* (2013.01); *A61K 31/573* (2013.01); *A61K 31/664* (2013.01); *A61K 31/704* (2013.01); *A61K 45/06* (2013.01)

(58) Field of Classification Search
CPC ... A61K 31/5377; A61K 31/506; A61K 45/06
See application file for complete search history.

(56) References Cited

U.S. PATENT DOCUMENTS

| | | |
|---|---|---|
| 6,660,733 B2 | 12/2003 | Sun et al. |
| 6,858,606 B2 | 2/2005 | Sun et al. |
| 7,863,270 B2 | 1/2011 | Demko et al. |
| 7,923,557 B2 | 4/2011 | Zhang et al. |

FOREIGN PATENT DOCUMENTS

| | | |
|---|---|---|
| WO | WO-2006/128129 A2 | 11/2006 |
| WO | WO-2006/128129 A3 | 11/2006 |
| WO | WO-2015/112888 A1 | 7/2015 |
| WO | WO-2017/015262 A1 | 1/2017 |
| WO | WO 2017/015262 A1 | 1/2017 |

OTHER PUBLICATIONS

Tycodi, S.S. Onco., Targets Ther., Jul. 2014, vol. 7, pp. 1349-1359.*
Bryan, J. The Pharmaceutical Journal, Aug. 2010, pp. 1349-1359.*
Baird, A.M. et al. (Jun. 19, 2013). "IL-23R is Epigenetically Regulated and Modulated by Chemotherapy in Non-Small Cell Lung Cancer," *Frontiers in Oncology* 3:162.
Cai, X. et al. (Jul. 25, 2013). "PIKfyve, a Class III PI Kinase, Is the Target of the Small Molecular IL-12/IL-23 Inhibitor Apilimod and a Player in Toll-like Receptor Signaling," *Chemistry & Biology* 20(7):912-921.
Coronas, S. et al. (Jul. 25, 2008. e-published May 22, 2008). "Elevated levels of PtdIns5P in NPM-ALK transformed cells: implication of PIKfyve," *Biochem Biophys Res Commun* 372(2):351-355.
International Search Report dated Sep. 26, 2016, for PCT Application No. PCT/US2016/042905, filed Jul. 19, 2016, 6 pages.
Krauz, S. et al. (Jun. 2012, e-published Dec. 14, 2011). "Brief report: a phase IIa, randomized, double-blind, placebo-controlled trial of apilimod mesylate, an interleukin-12/interleukin-23 inhibitor, in patients with rheumatoid arthritis," *Arthritis & Rheumatism* 64(6):1750-1755.
La Plante, M. et al. (Apr. 13, 2012), "mTOR signaling in growth control and disease" *Cell* 149(2):274-293.
Wada, Y. et al. (Feb. 1, 2007, e-published Oct. 19, 2006). "Selective abrogation of Th1 response by STA-5326, a potent IL-12/IL-23 inhibitor.," *Blood* 109(3):1156-1164.
Wada, Y. et al. (2012, e-published Apr. 6, 2012). "Apilimod inhibits the production of IL-12 and IL-23 and reduces dendritic cell infiltration in psoriasis." *PLosOne* 7(4):e35069.
Written Opinion dated Sep. 26, 2016, for PCT Application No. PCT/US2016/042905, filed Jul. 19, 2016, 7 pages.
Cao, S-S. et al. (1989). "Potentiation of antimetabolite antitumore activity in vivo by dipyridamole amphotericin B." *Cancer Chemother. Pharmacol.* 24:181-186.
Chen, F-H. et al. (2012). "LYG-202 augments tumor necrosis factor-α-induced apoptosis via attenuating caein kinase 2-dependent nuclear factor-κ-B pathway in HepG2 cells." *Mol. Phamacol.* 82:958-971.
Feng, J. et al. (2018). "The synergistic effects of Apatinib combined with cyctotoxic chemotherapeutic agents on gastric cancer cells and in a fluorescence imaging gastric cancer xenograft model" *Onco Targets and Therapy* 11:3047-3057.

(Continued)

*Primary Examiner* — Samira J Jean-Louis
(74) *Attorney, Agent, or Firm* — Muriel Liberto, Esq.; Mintz Levin Cohn Ferris Glovsky and Popeo, P.C.

(57) ABSTRACT

The present invention relates to methods for treating cancer with apilimod and related compositions and methods.

4 Claims, 13 Drawing Sheets

(56) References Cited

OTHER PUBLICATIONS

Shin, S-Y. et al. (Jun. 19, 2018). "Systems modelling of the EGFR-PYK2-c-Met Interaction network predicts and prioritizes synergistic drug combinations for triple-negative breast cancer." *PLOS Computional. Biol.* https://doi.org/10.1371/journal.pcbi. 1006192, S2: Model-based computation of drug synergy index. (32 pages).
Chou, T-C., (Jan. 12, 2010). "Drug combination studies and their synergy quantification using the Chou-Talalay method" *Cancer Research* 70(2):440-446.
Foucquier, J. et al. (Apr. 2, 2015). Analysis of drug combinations: current methodological landscape. *Pharmacol. Res. Perspectives* 3(3): e00129. doi: 10.1002/prp2.149.

\* cited by examiner

Kd = 75 pM

METHODS FOR TREATING CANCER USING APILIMOD

FIELD OF THE INVENTION

The present invention relates to compositions comprising apilimod and methods of using same.

BACKGROUND OF THE INVENTION

Apilimod, also referred to as STA-5326, hereinafter "apilimod", is recognized as a potent transcriptional inhibitor of IL-12 and IL-23. See e.g., Wada et al. *Blood* 109 (2007): 1156-1164. IL-12 and IL-23 are inflammatory cytokines normally produced by immune cells, such as B-cells and macrophages, in response to antigenic stimulation. Autoimmune disorders and other disorders characterized by chronic inflammation are characterized in part by inappropriate production of these cytokines. In immune cells, the selective inhibition of IL-12/IL-23 transcription by apilimod was recently shown to be mediated by apilimod's direct binding to phosphatidylinositol-3-phosphate 5-kinase (PIKfyve). See, e.g., Cai et al. *Chemistry and Biol.* 20 (2013):912-921. PIKfyve plays a role in Toll-like receptor signaling, which is important in innate immunity.

Based upon its activity as an immunomodulatory agent and a specific inhibitor of IL-12/IL-23, apilimod has been proposed as useful in treating autoimmune and inflammatory diseases and disorders. See e.g., U.S. Pat. Nos. 6,858,606 and 6,660,733 (describing a family of pyrimidine compounds, including apilimod, purportedly useful for treating diseases and disorders characterized by IL-12 or IL-23 overproduction, such as rheumatoid arthritis, sepsis, Crohn's disease, multiple sclerosis, psoriasis, or insulin dependent diabetes mellitus). Similarly, apilimod was suggested to be useful for treating certain cancers based upon its activity to inhibit c-Rel or IL-12/23, particularly in cancers where these cytokines were believed to play a role in promoting aberrant cell proliferation. See e.g., WO 2006/128129 and Baird et al., *Frontiers in Oncology* 3:1 (2013, respectively).

Each of three clinical trials of apilimod has focused on its potential efficacy in autoimmune and inflammatory diseases. The trials were conducted in patients having psoriasis, rheumatoid arthritis, and Crohn's disease. An open label clinical study in patients with psoriasis concluded that oral administration of apilimod showed immunomodulatory activity supporting the inhibition of IL-12/IL-23 synthesis for the treatment of TH1- and TH17-mediated inflammatory diseases. Wada et al., *PLosOne* 7:e35069 (April 2012). But the results of controlled trials in rheumatoid arthritis and Crohn's disease did not support the notion that IL-12/IL-23 inhibition by apilimod translates into clinical improvement in either of these indications. In a randomized, double-blind, placebo-controlled Phase II clinical trial of apilimod in patients with rheumatoid arthritis, apilimod failed to alter synovial IL-12 and IL-23 expression. Krauz et al., *Arthritis & Rheumatism* 64:1750-1755 (2012). The authors concluded that the "results do not support the notion the IL-12/IL-23 inhibition by apilimod is able to induce robust clinical improvement in RA." Similarly, a randomized, double-blind, placebo-controlled trial of apilimod for treatment of active Crohn's disease concluded that, although well tolerated, apilimod did not demonstrate efficacy over placebo. Sands et al *Inflamm Bowel Dis.* 2010 July; 16(7): 1209-18.

The mammalian target of rapamycin (mTOR) pathway is an important cellular signaling pathway that is involved in multiple physiological functions, including cell growth, cell proliferation, metabolism, protein synthesis, and autophagy (La Plante et al *Cell* 2012, (149 (2), pp. 274-293). mTOR is a kinase that integrates intracellular and extracellular cues that signal the levels of amino acids, stress, oxygen, energy, and growth factors and regulates the cellular response to these environment cues. mTOR deregulation has been implicated in a wide range of disorders and diseases, including cancer, obesity, diabetes, and neurodegeneration. Certain components of the mTOR pathway have been explored as drug targets for treating some of these diseases. However, therapeutic efficacy has been limited, for example, in the treatment of some cancers, and some mTOR inhibitors have been shown to have an adverse effect on metabolism. The tuberous sclerosis complex tumor suppressor genes, TSC1 and TSC2, are negative regulators of mTOR.

SUMMARY OF THE INVENTION

The present invention is based in part on the surprising discovery that apilimod is a highly cytotoxic agent in TSC null cells. In these cells, the mTOR pathway is constitutively active. The mTOR pathway is activated in a number of cancers, and in further screening of over 100 cancer cell lines apilimod showed anti-proliferative activity in cell lines from diverse cancers. Among the apilimod sensitive cancer cell lines, B-cell lymphomas were the most sensitive. But, unexpectedly, the differential sensitivity of B cell lymphomas to apilimod did not correlate with c-Rel expression, IL-12 expression, or IL-23 expression in these cells. This was surprising because earlier work had suggested apilimod would be useful against cancers where c-Rel and/or IL-12/23 expression were critical in promoting aberrant cell proliferation. Instead, the present inventors demonstrated that apilimod's cytotoxic activity in cancer cells was due to an inhibition of intracellular trafficking and a corresponding increase in apoptosis. This activity was not predicted based upon apilimod's immunomodulatory activity via its inhibition of IL-12/23 production. In addition, a screen of over 450 kinases identified PIKfyve as the only high affinity binding target (Kd=75 pM) for apilimod in a human cancer cell line.

The present invention provides new methods for the therapeutic use of apilimod in treating cancer, and particularly in treating B cell lymphomas, and especially those that are resistant or refractory to standard chemotherapy regimens.

In one embodiment, the invention provides a method for treating cancer in a subject in need thereof, the method comprising administering to the subject a composition comprising apilimod in an amount effective to inhibit cellular PIKfyve activity in the cancer cells of the subject. In one embodiment, the subject is human.

In one embodiment, the cancer is a brain cancer, a glioma, a sarcoma, breast cancer, lung cancer, non-small-cell lung cancer, mesothelioma, appendiceal cancer, a genitourinary cancer, a renal cell carcinoma, prostate cancer, bladder cancer, testicular cancer, penile cancer, cervical cancer, ovarian cancer, von Hippel Lindau disease, a head and neck cancer, a gastrointestinal cancer, a hepatocellular carcinoma, gallbladder cancer, esophageal cancer, gastric cancer, colorectal cancer, pancreatic cancer, a neuroendocrine tumor, a thyroid tumor, a pituitary tumor, an adrenal tumor, a hematological malignancy, a lymphoma, or a leukemia. In one embodiment, the cancer is a lymphoma and in a further embodiment, the cancer is a non-Hodgkin's lymphoma.

In one embodiment, the cancer is selected from DLBCL, follicular lymphoma, marginal zone lymphoma (MZL), CLL/SLL (Chronic lymphocytic leukemia/small lymphocytic lymphoma) and mantle cell lymphoma.

In one embodiment, the administering step is performed in at least one cycle consisting of at least 1 day of administering the composition comprising apilimod followed by at least 1 sequential day of not administering the composition comprising apilimod. In certain embodiments the administering step is performed in from 2 to 10 cycles or from 2 to 5 cycles. In one embodiment, a cycle consists of from 1 to 10 sequential days of administering the composition followed by from 1 to 5 sequential days of not administering the composition. In another embodiment, a cycle consists of from 2 to 5 sequential days of administering the composition followed by from 1 to 2 sequential days of not administering the composition. In a further embodiment, a cycle consists of 5 sequential days of administering the composition followed by 2 sequential days of not administering the composition.

In particular embodiments, the present invention provides methods for treating cancer using apilimod in a regimen that consists of 5 days of treatment with apilimod followed by 2 days off treatment in a 28-day cycle for a period of time ranging from 1 to 2 months, 1 to 3 months, 1 to 4 months, 1 to 5 months, 1 to 6 months, or from 6 to 12 months. Other embodiments are described below and in more detail infra.

In one aspect, the present invention provides a method for treating cancer in a subject in need thereof, the method comprising administering to the subject a therapeutically effective amount of an apilimod composition of the invention, said composition comprising apilimod, or a pharmaceutically acceptable salt, solvate, clathrate, hydrate, polymorph, prodrug, analog or derivative thereof. In one embodiment, the method comprises administering to the subject a composition comprising apilimod in an amount effective to inhibit cellular PIKfyve activity in the cancer cells of the subject. In one embodiment, the apilimod composition comprises apilimod free base or apilimod dimesylate.

In one embodiment, the method further comprises administering at least one additional active agent to the subject. The at least one additional active agent may be a therapeutic agent or a non-therapeutic agent. The at least one additional active agent may be administered in a single dosage form with the apilimod composition, or in a separate dosage form from the apilimod composition. In one embodiment, the at least one additional active agent is selected from the group consisting of an alkylating agent, an intercalating agent, a tublin binding agent, a corticosteroid, and combinations thereof.

In one embodiment, the at least one additional agent is an inhibitor of the checkpoint signaling pathway involving the programmed death 1 (PD-1) receptor and its ligands (PD-L1/2). In one embodiment, the method comprises a combination of an anti-PD-L1 agent and an anti-PD-1 agent. In one embodiment, the inhibitor is an anti-PD-L1 agent selected from BMS-936559/MDX-1105 (a fully human, high affinity, immunoglobulin (Ig) G4 monoclonal antibody to PD-L1), MPDL3280A (an engineered human monoclonal antibody targeting PD-L1), MSB0010718C and MEDI473. In one embodiment, the inhibitor is an anti-PD-1 agent selected from CT-011/pidilizumab, BMS-936558/MDX-1106/nivolumab, and pembrolizumab. In one embodiment, the inhibitor is selected from BMS-936559/MDX-1105, MPDL3280A, MSB0010718C, MEDI473, CT-011/pidilizumab, BMS-936558/MDX-1106/nivolumab, and pembrolizumab, and combinations of two or more of any of the foregoing.

In one embodiment, the at least one additional active agent is a therapeutic agent selected from the group consisting of ibrutinib, rituximab, doxorubicin, prednisolone, vincristine, velcade, and everolimus, and combinations thereof. In one embodiment, the at least one additional active agent is a therapeutic agent selected from cyclophosphamide, hydroxydaunorubicin (also referred to as doxorubicin or Adriamycin™), vincristine (also referred to as Oncovin™), prednisone, prednisolone, and combinations thereof. In one embodiment, the at least one additional active agent is a therapeutic agent selected from the group consisting of BMS-936559/MDX-1105, MPDL3280A, MSB0010718C, MEDI473, CT-011/pidilizumab, BMS-936558/MDX-1106/nivolumab, and pembrolizumab, and combinations of two or more of any of the foregoing.

In one embodiment, the at least one additional active agent is a non-therapeutic agent. In one embodiment, the non-therapeutic agent is selected to ameliorate one or more side effects of the apilimod composition. In one embodiment, the non-therapeutic agent is selected from the group consisting of ondansetron, granisetron, dolasetron and palonosetron. In one embodiment, the non-therapeutic agent is selected from the group consisting of pindolol and risperidone. In one embodiment, the non-therapeutic agent is selected to increase the bioavailability of the apilimod in the apilimod composition. In one aspect of this embodiment, the non-therapeutic agent is a CYP3A inhibitor. In a particular embodiment, the CYP3A inhibitor is ritonavir or cobicistat.

In one embodiment, the dosage form of the apilimod composition is an oral dosage form. In another embodiment, the dosage form of the apilimod composition is suitable for intravenous administration. In one embodiment, where the dosage form is suitable for intravenous administration, administration is by a single injection or by a drip bag.

In one embodiment, the subject is a human cancer patient. In one embodiment, the human cancer patient in need of treatment with an apilimod composition of the invention is one whose cancer is refractory to a standard chemotherapy regimen. In one embodiment, the human cancer patient in need of treatment with an apilimod composition is one whose cancer has recurred following treatment with a standard chemotherapy regimen. In one embodiment, the cancer is a lymphoma. In one embodiment, the cancer is a B cell lymphoma. In one embodiment, the B cell lymphoma is a non-Hodgkin's B cell lymphoma. In one embodiment, the non-Hodgkin's B cell lymphoma is selected from a diffuse large B cell lymphoma (DLBCL), a Burkitt's lymphoma, a mediastinal B cell lymphoma, a mantle cell lymphoma, and a follicular lymphoma. In one embodiment, the non-Hodgkin's B cell lymphoma is DLBCL. In one embodiment, the DLBCL is the GCB subtype.

In one embodiment, the standard chemotherapy regimen comprises one or more therapeutic agents selected from the group consisting of ibrutinib, rituximab, doxorubicin, prednisolone, vincristine, velcade, cyclophosphoamide, dexamethasone and everolimus. In one embodiment, the standard chemotherapy regimen is selected from CHOP, (cyclophosphamide, hydroxydaunorubicin, Oncovin™ (vincristine), and prednisone or prednisolone), COOP (cyclophosamide, vincristine sulfate, procarbazine hydrochloride, prednisone), CVP (cyclophosamide, vincristine sulfate, prednisone), EPOCH (etoposide, prednisone, vincristine sulfate, cyclophosphamide, doxorubicin hydrochloride), Hyper-CVAD (cyclophosphamide, vincristine sulfate, doxorubicin hydrochloride, dexamethasone), ICE (ifosfamide, carboplatin, etoposide), R-CHOP (rituximab, cyclophosphamide, vincristine sulfate, procarbazine hydrochloride, prednisone, and R-CVP (rituximab, cyclophosamide, vincristine sulfate, prednisone).

In one embodiment, the method is a method of treating a lymphoma using a combination therapy comprising an apilimod composition and a chemotherapy regimen for the treatment of the lymphoma. In one embodiment, the chemotherapy regimen is the CHOP regimen. In another embodiment, the chemotherapy regimen is selected from COOP, CVP, EPOCH, Hyper-CVAD, ICE, R-CHOP, and R-CVP. The regimen may also include one or more additional non-therapeutic agents as described above, for example a non-therapeutic agent selected from one or more of a CYP3A inhibitor such as ritonavir or cobicistat, ondansetron, granisetron, dolasetron, palonosetron, pindolol and risperidone.

DETAILED DESCRIPTION OF THE INVENTION

Figure 1A:
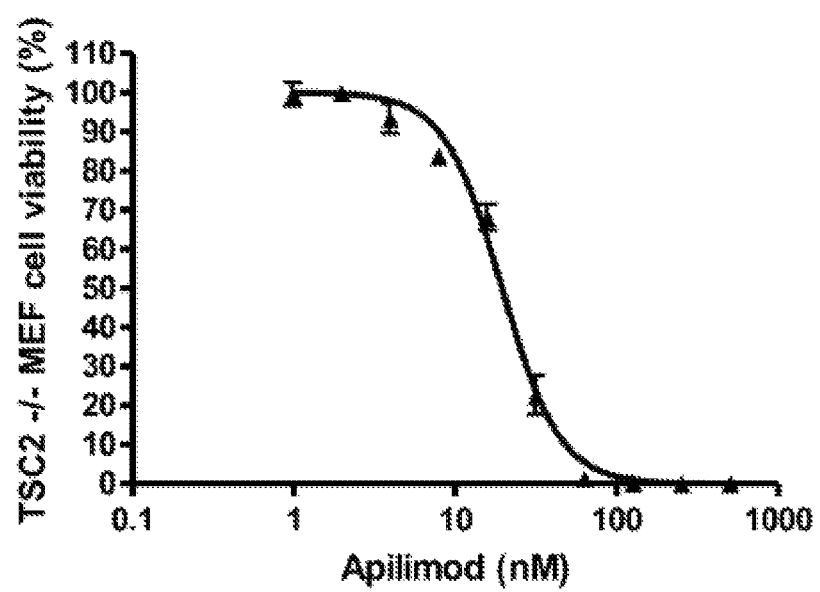
FIG. 1A: TSC2 deficient cells are highly sensitive to apilimod ($IC_{50}$=19.5 nM).

The present invention provides compositions and methods related to the use of apilimod for treating cancer in a subject, preferably a human subject, in need of such treatment. The present invention generally relates to new uses of apilimod based upon the surprising discovery of apilimod's cytotoxic activity against a range of cancer cells of both lymphoid and non-lymphoid origin, an activity that is not clearly related to, or predictable from, apilimod's known immunomodulatory and IL-12/23 inhibitory activity. In addition, the present invention provides novel therapeutic approaches to cancer treatment based upon therapeutic regimens utilizing apilimod either alone, as monotherapy, or in combination with at least one additional therapeutic agent, such as an additional anti-cancer (chemotherapeutic) agent. The therapeutic regimens described here exploit the selective cytotoxic activity of apilimod against cancer cells compared to non-cancer (normal) cells as well as the increased sensitivity of cancer cells to apilimod administered over a period of time.

As used herein, the term "an apilimod composition" may refer to a composition comprising apilimod itself (free base), or may encompass pharmaceutically acceptable salts, solvates, clathrates, hydrates, polymorphs, prodrugs, analogs or derivatives of apilimod, as described below. The structure of apilimod is shown in Formula I:

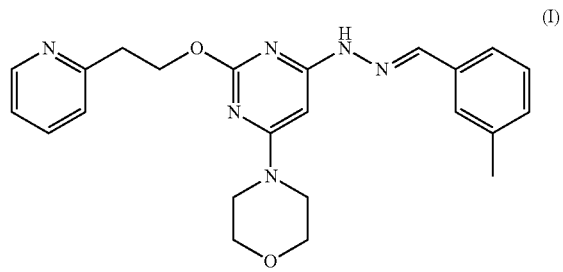 [SMILES: Cc1cccc(/C=N/Nc2cc(N3CCOCC3)nc(OCCc3ccccn3)n2)c1]

The chemical name of apilimod is 2-[2-Pyridin-2-yl)-ethoxy]-4-N'-(3-methyl-benzilidene)-hydrazino]-6-(morpholin-4-yl)-pyrimidine (IUPAC name: (E)-4-(6-(2-(3-methylbenzylidene)hydrazinyl)-2-(2-(pyridin-2-yl)ethoxy)pyrimidin-4-yl)morpholine), and the CAS number is 541550-19-0.

Apilimod can be prepared, for example, according to the methods described in U.S. Pat. Nos. 7,923,557, and 7,863,270, and WO 2006/128129.

As used herein, the term "pharmaceutically acceptable salt," is a salt formed from, for example, an acid and a basic group of an apilimod composition. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (e.g., 1,1'-methylene-bis- (2-hydroxy-3-naphthoate)) salts. In a preferred embodiment, the salt of apilimod comprises methanesulfonate.

The term "pharmaceutically acceptable salt" also refers to a salt prepared from an apilimod composition having an acidic functional group, such as a carboxylic acid functional group, and a pharmaceutically acceptable inorganic or organic base.

The term "pharmaceutically acceptable salt" also refers to a salt prepared from an apilimod composition having a basic functional group, such as an amino functional group, and a pharmaceutically acceptable inorganic or organic acid.

The salts of the compounds described herein can be synthesized from the parent compound by conventional chemical methods such as methods described in Pharmaceutical Salts: Properties, Selection, and Use, P. Hemrich Stahl (Editor), Camille G. Wermuth (Editor), ISBN: 3-90639-026-8, August 2002. Generally, such salts can be prepared by reacting the parent compound with the appropriate acid in water or in an organic solvent, or in a mixture of the two.

One salt form of a compound described herein can be converted to the free base and optionally to another salt form by methods well known to the skilled person. For example, the free base can be formed by passing the salt solution through a column containing an amine stationary phase (e.g. a Strata-$NH_2$ column). Alternatively, a solution of the salt in water can be treated with sodium bicarbonate to decompose the salt and precipitate out the free base. The free base may then be combined with another acid using routine methods.

As used herein, the term "polymorph" means solid crystalline forms of a compound of the present invention (e.g., 2-[2-Pyridin-2-yl)-ethoxy]-4-N'-(3-methyl -benzilidene)-hydrazino]-6-(morpholin-4-yl)-pyrimidine) or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "hydrate" means a compound of the present invention (e.g., 2-[2-Pyridin-2-yl)-ethoxy]-4-N'-(3-methyl-benzilidene)-hydrazino]-6-(morpholin-4-yl)-pyrimidine) or a salt thereof, which further includes a stoichiometric or non-stoichiometric amount of water bound by non-covalent intermolecular forces.

As used herein, the term "clathrate" means a compound of the present invention (e.g., 2-[2-Pyridin-2-yl)-ethoxy]-4-N'-(3-methyl-benzilidene)-hydrazino]-6-(morpholin-4-yl)-pyrimidine) or a salt thereof in the form of a crystal lattice that contains spaces (e.g., channels) that have a guest molecule (e.g., a solvent or water) trapped within.

As used herein, the term "prodrug" means a derivative of a compound described herein (e.g., 2-[2-Pyridin-2-yl)-ethoxy]-4-N'-(3-methyl-benzilidene)-hydrazino]-6-(morpholin-4-yl)-pyrimidine) that can hydrolyze, oxidize, or otherwise react under biological conditions (in vitro or in vivo) to provide a compound of the invention. Prodrugs may only become active upon such reaction under biological conditions, or they may have activity in their unreacted forms. Examples of prodrugs contemplated in this invention include, but are not limited to, analogs or derivatives of a compound described herein (e.g., 2-[2-Pyridin-2-yl)-ethoxy]-4-N'-(3-methyl-benzilidene)-hydrazino]-6-(morpholin-4-yl)-pyrimidine) that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —$NO_2$, —ONO, or —$ONO_2$ moieties. Prodrugs can typically be prepared using well-known methods, such as those described by Burger's Medicinal Chemistry and Drug Discovery (1995) 172-178, 949-982 (Manfred E. Wolff ed., 5th ed).

As used herein, the term "solvate" or "pharmaceutically acceptable solvate," is a solvate formed from the association of one or more solvent molecules to one of the compounds disclosed herein (e.g., 2-[2-Pyridin-2-yl)-ethoxy]-4-N'-(3-methyl-benzilidene)-hydrazino]-6-(morpholin-4-yl)-pyrimidine). The term solvate includes hydrates (e.g., hemi-hydrate, mono-hydrate, dihydrate, trihydrate, tetrahydrate, and the like).

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound. As used herein, the term "derivative" refers to compounds that have a common core structure, and are substituted with various groups as described herein.

Methods of Treatment

The present invention provides methods for the treatment of cancer in a subject in need thereof by administering to the subject a therapeutically effective amount of an apilimod composition of the invention, said composition comprising apilimod, or a pharmaceutically acceptable salt, solvate, clathrate, hydrate, polymorph, prodrug, analog or derivative thereof. In one embodiment, the apilimod composition comprises apilimod free base or apilimod dimesylate. The present invention further provides the use of an apilimod composition for the preparation of a medicament useful for the treatment of cancer.

In one embodiment, the cancer is brain cancer, glioma, sarcoma, breast cancer, lung cancer, non-small-cell lung cancer, mesothelioma, appendiceal cancer, genitourinary cancers, renal cell carcinoma, prostate cancer, bladder cancer, testicular cancer, penile cancer, cervical cancer, ovarian cancer, von Hippel Lindau disease, head and neck cancer, gastrointestinal cancer, hepatocellular carcinoma, gallbladder cancer, esophageal cancer, gastric cancer, colorectal cancer, pancreatic cancer, neuroendocrine tumors, thyroid tumor, pituitary tumor, adrenal tumor, hematological malignancy, or leukemia.

In one embodiment the cancer is a lymphoma. In one embodiment, the lymphoma is a B cell lymphoma. In one embodiment, the B cell lymphoma is selected from the group consisting of a Hodgkin's B cell lymphoma and a non-Hodgkin's B cell lymphoma. In one embodiment, the B cell lymphoma is a non-Hodgkin's B cell lymphoma selected from the group consisting of DLBCL, follicular lymphoma, marginal zone lymphoma (MZL) or mucosa associated lymphatic tissue lymphoma (MALT), small cell lymphocytic lymphoma (overlaps with chronic lymphocytic leukemia) and mantle cell lymphoma. In one embodiment, the B cell lymphoma is a non-Hodgkin's B cell lymphoma selected from the group consisting of Burkitt lymphoma, Burkitt lymphoma, primary mediastinal (thymic) large B-cell lymphoma, lymphoplasmacytic lymphoma, which may manifest as Waldenström macroglobulinemia, nodal marginal zone B cell lymphoma (NMZL), splenic marginal zone lymphoma (SMZL), intravascular large B-cell lymphoma, primary effusion lymphoma, lymphomatoid granulomatosis, T cell/histiocyte-rich large B-cell lymphoma, primary central nervous system lymphoma, primary cutaneous diffuse large B-cell lymphoma, leg type (Primary cutaneous DLBCL, leg type), EBV positive diffuse large B-cell lymphoma of the elderly, Diffuse large B-cell lymphoma associated with inflammation, intravascular large B-cell lymphoma, ALK-positive large B-cell lymphoma, and plasmablastic lymphoma.

In one embodiment the cancer is a lymphoma selected from DLBCL, follicular lymphoma, marginal zone lymphoma (MZL), CLL/SLL (Chronic lymphocytic leukemia/small lymphocytic lymphoma) and mantle cell lymphoma.

In one embodiment, the method is a therapeutic regimen for treating a non-Hodgkins lymphoma (NHL) in a subject in need thereof. In one embodiment, the method comprising administering to the subject a daily amount of an apilimod composition effective to inhibit cellular PIKfyve activity in the cancer cells of the subject. In one embodiment, the apilimod composition is administered in a regimen that consists of at least 1 day of administering the composition comprising apilimod followed by at least 1 sequential day of not administering the composition comprising apilimod. In one embodiment, the administering step is performed in from 2 to 10 cycles or in from 2 to 5 cycles. In one embodiment, the cycle consists of from 1 to 10 sequential days of administering the composition followed by from 1 to 5 sequential days of not administering the composition. In one embodiment, the cycle consists of from 2 to 5 sequential days of administering the composition followed by from 1 to 2 sequential days of not administering the composition. In one embodiment, the cycle consists of 5 sequential days of administering the composition followed by 2 sequential days of not administering the composition.

In one embodiment, the method comprises or consists of 5 days of treatment with apilimod followed by 2 days off treatment in a 28-day cycle for a period of time ranging from 1 to 2 months, 1 to 3 months, 1 to 4 months, 1 to 5 months, 1 to 6 months, or from 6 to 12 months.

In accordance with any of these embodiments, the apilimod composition may comprise apilimod free base or apilimod dimesylate. In one embodiment the NHL is a follicular lymphoma. In one embodiment, the NHL is a mantel cell lymphoma. In one embodiment the NHL is a Burkitt's lymphoma. In one embodiment, the NHL is a diffuse large B cell lymphoma (DLBCL), a Burkitt's lymphoma, a mediastinal B cell lymphoma, or a mantle cell lymphoma. In one embodiment, the NHL is a DLBCL. In one embodiment, the DLBCL is refractory. In one embodiment, the refractory DLBCL is a DLBCL-ABC or a DLBCL-GCB. In one embodiment, the refractory DLBCL contains a double myc/bcl2 translocation ("double-hit DLBCL"). In one embodiment the DLBCL is refractory to standard CHOP treatment.

Combination Therapy

The present invention also provides methods comprising combination therapy. As used herein, "combination therapy" or "co-therapy" includes the administration of a therapeutically effective amount of an apilimod composition with at least one additional active agent, as part of a specific treatment regimen intended to provide a beneficial effect from the co-action of the apilimod composition and the additional active agent. "Combination therapy" is not intended to encompass the administration of two or more therapeutic compounds as part of separate monotherapy regimens that incidentally and arbitrarily result in a beneficial effect that was not intended or predicted.

In one embodiment, the method is a method of treating cancer using a combination therapy comprising an apilimod composition and a chemotherapy regimen for the treatment of cancer. In one embodiment, the chemotherapy regimen is the CHOP regimen. CHOP refers to a regimen generally used in the treatment of non-Hodgkin's lymphoma consisting of the following active agents: (C)yclophosphamide, an alkylating agent which damages DNA by binding to it and causing the formation of cross-links; (H)ydroxydaunorubicin (also called doxorubicin or Adriamycin), an intercalating agent which damages DNA by inserting itself between DNA bases; (O)ncovin (vincristine), which prevents cells from duplicating by binding to the protein tubulin; and (P)rednisone or (P)rednisolone, which are corticosteroids. In another embodiment, the chemotherapy regimen is selected from COOP (cyclophosamide, vincristine sulfate, procarbazine hydrochloride, prednisone), CVP (cyclophosamide, vincristine sulfate, prednisone), EPOCH (etoposide, prednisone, vincristine sulfate, cyclophosphamide, doxorubicin hydrochloride), Hyper-CVAD (cyclophosphamide, vincristine sulfate, doxorubicin hydrochloride, dexamethasone), ICE (ifosfamide, carboplatin, etoposide), R-CHOP (rituximab, cyclophosamide, vincristine sulfate, procarbazine hydrochloride, prednisone, and R-CVP (rituximab, cyclophosamide, vincristine sulfate, prednisone).

The at least one additional active agent may be a therapeutic agent, for example an anti-cancer agent or a cancer chemotherapeutic agent, or a non-therapeutic agent, and combinations thereof. With respect to therapeutic agents, the beneficial effect of the combination includes, but is not limited to, pharmacokinetic or pharmacodynamic co-action resulting from the combination of therapeutically active compounds. With respect to non-therapeutic agents, the beneficial effect of the combination may relate to the mitigation of a toxicity, side effect, or adverse event associated with a therapeutically active agent in the combination.

In one embodiment, the at least one additional agent is a non-therapeutic agent which mitigates one or more side effects of an apilimod composition, the one or more side effects selected from any of nausea, vomiting, headache, dizziness, lightheadedness, drowsiness and stress. In one aspect of this embodiment, the non-therapeutic agent is an antagonist of a serotonin receptor, also known as 5-hydroxytryptamine receptors or 5-HT receptors. In one aspect, the non-therapeutic agent is an antagonist of a $5-HT_3$ or $5-HT_{1a}$ receptor. In one aspect, the non-therapeutic agent is selected from the group consisting of ondansetron, granisetron, dolasetron and palonosetron. In another aspect, the non-therapeutic agent is selected from the group consisting of pindolol and risperidone.

In one embodiment, the at least one additional agent is a therapeutic agent. In one embodiment, the therapeutic agent is an anti-cancer agent. In one embodiment, the anti-cancer agent is ibrutinib. In one embodiment, an apilimod composition is administered along with ibrutinib in a single dosage form or in separate dosage forms. In one embodiment, the dosage form is an oral dosage form. In another embodiment, the dosage form is suitable for intravenous administration.

In one embodiment, the anti-cancer agent is a drug that is approved for use in treating lymphoma. Non-limiting examples of such drugs include abitrexate (methotrexate), adcetris (brentuximab vedotin), ambochlorin (chlorambucil), amboclorin (chloramucil), arranon (nelarabine), becenum (carmustine), beleodaq (belinostat), belinostat, bendamustine hydrochloride, bexxar (tositumomab and Iodine I 131 tositumomab), BiCNU (carmustine), blenoxane (bleomycin), bleomycin, bortezomib, brentuximab vedotin, carmubris (carmustine), carmustine, chlorambucil, clafen (cyclophosphamide), cyclophosphamide, cytoxan (cyclophosphamide), denileukin diftitox, DepoCyt (liposomal cytarabine), doxorubicin hydrochloride, folex (methotrexate), folotyn (pralatrexate), ibritumomab tiuxetan, ibrutinib, idelalisib, imbruvica (ibtrutinib), intron A (recombinant interferon Alfa-2b), istodax (romidepsin), lenalidomide, leukeran (chlorambucil), linfolizin (chlorambucil), liposomal cytarabine, mechlorethamine hydrochloride, methotrexate, methotrexate LPF (methotrexate), mexate (methotrexate), mexate -AQ (methotrexate), mozobil (perixafor), mustargen (mechlorethamine hydrochloride), nelarabine, neosar (cyclophosphamide), ontak (denifleukin diftitox), perixafor, pralatrexate, prednisone, recombinant interferon Alfa-2b, revlimid (lenalidomide), rituxan (rituximab), rituximab, romidepsin, tositumomab and iodine I 131 tositumomab, treanda (bendamustine hydrochloride), velban (vinblastine sulfate), velcade (bortezomib), velsar (vinblasinte sulfate), vinblastine sulfate, vincasar PFS (vincristine sulfate), vincristine sulfate, vorinostat, zevalin (ibritumomab triuxetan), zolinza (vorinostat), and zydelig (idelalisib).

In one embodiment, the anti-cancer agent is selected from an inhibitor of EZH2, e.g., EPZ-6438. In one embodiment, the anti-cancer agent is selected from taxol, vincristine, doxorubicin, temsirolimus, carboplatin, ofatumumab, rituximab, and combinations thereof.

In one embodiment, the at least one additional agent is a B cell receptor pathway inhibitor. In some embodiments, the B cell receptor pathway inhibitor is a CD79A inhibitor, a CD79B inhibitor, a CD 19 inhibitor, a Lyn inhibitor, a Syk inhibitor, a PI3K inhibitor, a Blnk inhibitor, a PLCy inhibitor, a PKCP inhibitor, or a combination thereof. In some embodiments, the at least one additional agent is an antibody, B cell receptor signaling inhibitor, a PI3K inhibitor, an IAP inhibitor, an mTOR inhibitor, a radioimmunotherapeutic, a DNA damaging agent, a proteosome inhibitor, a histone deacetylase inhibitor, a protein kinase inhibitor, a hedgehog inhibitor, an Hsp90 inhibitor, a telomerase inhibitor, a Jakl/2 inhibitor, a protease inhibitor, a PKC inhibitor, a PARP inhibitor, or a combination thereof.

In one embodiment, the at least one additional agent is selected from chlorambucil, ifosphamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof.

In one embodiment, the at least one additional agent is a monoclonal antibody such as, for example, alemtuzumab, bevacizumab, catumaxomab, cetuximab, edrecolomab, gemtuzumab, ofatumumab, panitumumab, rituximab, trastuzumab, eculizumab, efalizumab, muromab-CD3, natalizumab, adalimumab, afelimomab, certolizumab pegol, golimumab, infliximab, basiliximab, canakinumab, daclizumab, mepolizumab, tocilizumab, ustekinumab, ibritumomab tiuxetan, tositumomab, abagovomab, adecatumumab, alemtuzumab, anti-CD30 monoclonal antibody Xmab2513, anti-MET monoclonal antibody MetMab, apolizumab, apomab, arcitumomab, basiliximab, bispecific antibody 2B1, blinatumomab, brentuximab vedotin, capromab pendetide, cixutumumab, claudiximab, conatumumab, dacetuzumab, denosumab, eculizumab, epratuzumab, ertumaxomab, etaracizumab, figitumumab, fresolimumab, galiximab, ganitumab, gemtuzumab ozogamicin, glembatumumab, ibritumomab, inotuzumab ozogamicin, ipilimumab, lexatumumab, lintuzumab, lintuzumab, lucatumumab, mapatumumab, matuzumab, milatuzumab, monoclonal antibody CC49, necitumumab, nimotuzumab, ofatumumab, oregovomab, pertuzumab, ramacurimab, ranibizumab, siplizumab, sonepcizumab, tanezumab, tositumomab, trastuzumab, tremelimumab, tucotuzumab celmoleukin, veltuzumab, visilizumab, volociximab, and zalutumumab.

In the context of combination therapy, administration of the apilimod composition may be simultaneous with or sequential to the administration of the one or more additional active agents. In another embodiment, administration of the different components of a combination therapy may be at different frequencies. The one or more additional agents may be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a compound of the present invention.

The one or more additional active agents can be formulated for co-administration with an apilimod composition in a single dosage form, as described in greater detail herein. The one or more additional active agents can be administered separately from the dosage form that comprises the compound of the present invention. When the additional active agent is administered separately from the apilimod composition, it can be by the same or a different route of administration as the apilimod composition.

Preferably, the administration of an apilimod composition in combination with one or more additional agents provides a synergistic response in the subject being treated. In this context, the term "synergistic" refers to the efficacy of the combination being more effective than the additive effects of either single therapy alone. The synergistic effect of a combination therapy according to the invention can permit the use of lower dosages and/or less frequent administration of at least one agent in the combination compared to its dose and/or frequency outside of the combination. Additional beneficial effects of the combination can be manifested in the avoidance or reduction of adverse or unwanted side effects associated with the use of either therapy in the combination alone (also referred to as monotherapy).

"Combination therapy" also embraces the administration of the compounds of the present invention in further combination with non-drug therapies (e.g., surgery or radiation treatment). Where the combination therapy further comprises a non-drug treatment, the non-drug treatment may be conducted at any suitable time so long as a beneficial effect from the co-action of the combination of the therapeutic compounds and non-drug treatment is achieved. For example, in appropriate cases, the beneficial effect is still achieved when the non-drug treatment is temporally removed from the administration of the therapeutic compounds, perhaps by days or even weeks.

The non-drug treatment can be selected from chemotherapy, radiation therapy, hormonal therapy, anti-estrogen therapy, gene therapy, and surgery. For example, a non-drug therapy is the removal of an ovary (e.g., to reduce the level of estrogen in the body), thoracentesis (e.g., to remove fluid from the chest), paracentesis (e.g., to remove fluid from the abdomen), surgery to remove or shrink angiomyolipomas, lung transplantation (and optionally with an antibiotic to prevent infection due to transplantation), or oxygen therapy (e.g., through a nasal cannula containing two small plastic tubes or prongs that are placed in both nostrils, through a face mask that fits over the nose and mouth, or through a small tube inserted into the windpipe through the front of the neck, also called transtracheal oxygen therapy).

In the context of the methods described herein, the amount of an apilimod composition administered to the subject is a therapeutically effective amount. The term "therapeutically effective amount" refers to an amount sufficient to treat, ameliorate a symptom of, reduce the severity of, or reduce the duration of the disease or disorder being treated, or enhance or improve the therapeutic effect of another therapy, or sufficient to exhibit a detectable therapeutic effect in the subject. In one embodiment, the therapeutically effective amount of an apilimod composition is the amount effective to inhibit PIKfyve kinase activity.

An effective amount of an apilimod composition can range from about 0.001 mg/kg to about 1000 mg/kg, about 0.01 mg/kg to about 100 mg/kg, about 10 mg/kg to about 250 mg/kg, about 0.1 mg/kg to about 15 mg/kg; or any range in which the low end of the range is any amount between 0.001 mg/kg and 900 mg/kg and the upper end of the range is any amount between 0.1 mg/kg and 1000 mg/kg (e.g., 0.005 mg/kg and 200 mg/kg, 0.5 mg/kg and 20 mg/kg). Effective doses will also vary, as recognized by those skilled in the art, depending on the diseases treated, route of administration, excipient usage, and the possibility of co-usage with other therapeutic treatments such as use of other agents. See, e.g., U.S. Pat. No. 7,863,270, incorporated herein by reference.

In more specific aspects, an apilimod composition is administered at a dosage regimen of 30-1000 mg/day (e.g., 30, 35, 40, 45, 50, 55, 60, 65, 70, 75, 80, 85, 90, 95, 100, 125, 150, 175, 200, 225, 250, 275, or 300 mg/day) for at least 1 week (e.g., 1, 2, 3, 4, 5, 6, 7, 8, 9, 10, 11, 12, 36, 48, or more weeks). Preferably, an apilimod composition is administered at a dosage regimen of 100-1000 mg/day for 4 or 16 weeks. Alternatively or subsequently, an apilimod composition is administered at a dosage regimen of 100 mg-300 mg twice a day for 8 weeks, or optionally, for 52 weeks. Alternatively or subsequently, an apilimod composition is administered at a dosage regimen of 50 mg-1000 mg twice a day for 8 weeks, or optionally, for 52 weeks.

An effective amount of the apilimod composition can be administered once daily or twice daily, or from two to five times daily, up to two times or up to three times daily, or up to eight times daily. In one embodiment, the apilimod composition is administered thrice daily, twice daily, once daily, fourteen days on (four times daily, thrice daily or twice daily, or once daily) and 7 days off in a 3-week cycle, up to five or seven days on (four times daily, thrice daily or twice daily, or once daily) and 14-16 days off in 3 week cycle, or once every two days, or once a week, or once every 2 weeks, or once every 3 weeks.

In one embodiment, the apilimod composition is administered once or twice daily in a regimen of 5 days on, 2 days off in a 28-day cycle for a period of time that is from 1-2 months, from 1-3 months, from 1-4 months, from 1-5 months, from 1-6 months, or from 6-12 months.

In accordance with the methods described herein, a "subject in need of" is a subject having a disease, disorder or condition, or a subject having an increased risk of developing a disease, disorder or condition relative to the population at large. The subject in need thereof can be one that is "non-responsive" or "refractory" to a currently available therapy for the disease or disorder, for example cancer. In this context, the terms "non-responsive" and "refractory" refer to the subject's response to therapy as not clinically adequate to relieve one or more symptoms associated with the disease or disorder. In one aspect of the methods described here, the subject in need thereof is a subject having cancer whose cancer is refractory to standard therapy or whose cancer has recurred following standard treatment.

A "subject" includes a mammal. The mammal can be e.g., any mammal, e.g., a human, primate, vertebrate, bird, mouse, rat, fowl, dog, cat, cow, horse, goat, camel, sheep or a pig. Preferably, the mammal is a human. The term "patient" refers to a human subject.

The present invention also provides a monotherapy for the treatment of a disease, disorder or condition as described herein. As used herein, "monotherapy" refers to the administration of a single active or therapeutic compound to a subject in need thereof.

As used herein, "treatment", "treating" or "treat" describes the management and care of a patient for the purpose of combating a disease, condition, or disorder and includes the administration of an apilimod composition to alleviate the symptoms or complications of a disease, condition or disorder, or to eliminate the disease, condition or disorder.

As used herein, "prevention", "preventing" or "prevent" describes reducing or eliminating the onset of the symptoms or complications of the disease, condition or disorder and includes the administration of an apilimod composition to reduce the onset, development or recurrence of symptoms of the disease, condition or disorder.

In one embodiment, the administration of an apilimod composition leads to the elimination of a symptom or complication of the disease or disorder being treated, however, elimination is not required. In one embodiment, the severity of the symptom is decreased. In the context of cancer, such symptoms may include clinical markers of severity or progression including the degree to which a tumor secrets growth factors, degrades the extracellular matrix, becomes vascularized, loses adhesion to juxtaposed tissues, or metastasizes, as well as the number of metastases.

Treating cancer according to the methods described herein can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer according to the methods described herein can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer according to the methods described herein can result in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer according to the methods described herein can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

As used herein, the term "selectively" means tending to occur at a higher frequency in one population than in another population. The compared populations can be cell populations. Preferably, an apilimod composition as described herein acts selectively on hyper-proliferating cells or abnormally proliferating cells, compared to normal cells. As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms. Preferably, an apilimod composition acts selectively to modulate one molecular target (e.g., a target kinase) but does not significantly modulate another molecular target (e.g., a non-target kinase). The invention also provides a method for selectively inhibiting the activity of an enzyme, such as a kinase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in diseased or hyper-proliferating cells if it occurred greater than twice as frequently in diseased or hyper-proliferating cells as compared to normal cells.

Pharmaceutical Compositions and Formulations

The present invention provides apilimod compositions that are preferably pharmaceutically acceptable compositions suitable for use in a mammal, preferably a human. In this context, the compositions may further comprise at least one pharmaceutically acceptable excipient or carrier, wherein the amount is effective for the treatment of a disease or disorder. In one embodiment, the disease or disorder is cancer, preferably a lymphoma, and most preferably a B cell lymphoma. In one embodiment, the disease or disorder is an mTOR disease or disorder.

In one embodiment, the apilimod composition comprises apilimod free base or apilimod dimesylate.

In one embodiment, the apilimod composition is combined with at least one additional active agent in a single dosage form. In one embodiment, the composition further comprises an antioxidant.

In one embodiment, the at least one additional active agent is selected from the group consisting of an alkylating agent, an intercalating agent, a tublin binding agent, a corticosteroid, and combinations thereof. In one embodiment, the at least one additional active agent is a therapeutic agent selected from the group consisting of ibrutinib, rituximab, doxorubicin, prednisolone, vincristine, velcade, and everolimus, and combinations thereof. In one embodiment, the at least one additional active agent is a therapeutic agent selected from cyclophosphamide, hydroxydaunorubicin (also referred to as doxorubicin or Adriamycin™), vincristine (also referred to as Oncovin™), prednisone, prednisolone, and combinations thereof. In one embodiment, the at least one additional active agent is a non-therapeutic agent selected to ameliorate one or more side effects of the apilimod composition. In one embodiment, the non-therapeutic agent is selected from the group consisting of ondansetron, granisetron, dolasetron and palonosetron. In one embodiment, the non-therapeutic agent is selected from the group consisting of pindolol and risperidone.

In one embodiment, the at least one additional active agent is selected from an inhibitor of the mTOR pathway, a PI3K inhibitor, a dual PI3K/mTOR inhibitor, a SRC inhibitor, a VEGF inhibitor, a Janus kinase (JAK) inhibitor, a Raf inhibitor, an Erk inhibitor, a farnesyltransferase inhibitor, a histone deacetylase inhibitor, an anti-mitotic agent, a multi-drug resistance efflux inhibitor, an antibiotic, and a therapeutic antibody. In one embodiment, the at least one additional active agent is selected from a farnesyltransferase inhibitor (e.g., tipifarnib), an anti-mitotic agent (e.g., docetaxel), a histone deacetylase inhibitor (e.g., vorinostat), and a multi-drug resistance efflux inhibitor.

In one embodiment, the anti-mitotic agent is selected from Griseofulvin, vinorelbine tartrate, paclitaxel, docetaxel, vincristine, vinblastine, Epothilone A, Epothilone B, ABT-751, CYT997 (Lexibulin), vinflunine tartrate, Fosbretabulin, GSK461364, ON-01910 (Rigosertib), Ro3280, BI2536, NMS-P937, BI 6727 (Volasertib), HMN-214 and MLN0905.

In one embodiment, the polyether antibiotic is selected from sodium monensin, nigericin, valinomycin, salinomycin.

A "pharmaceutical composition" is a formulation containing the compounds described herein in a pharmaceutically acceptable form suitable for administration to a subject. As used herein, the phrase "pharmaceutically acceptable" refers to those compounds, materials, compositions, carriers, and/ or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof.

A pharmaceutical composition can be provided in bulk or in dosage unit form. It is especially advantageous to formulate pharmaceutical compositions in dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved. A dosage unit form can be an ampoule, a vial, a suppository, a dragee, a tablet, a capsule, an IV bag, or a single pump on an aerosol inhaler.

In therapeutic applications, the dosages vary depending on the agent, the age, weight, and clinical condition of the recipient patient, and the experience and judgment of the clinician or practitioner administering the therapy, among other factors affecting the selected dosage. Generally, the dose should be a therapeutically effective amount. Dosages can be provided in mg/kg/day units of measurement (which dose may be adjusted for the patient's weight in kg, body surface area in $m^2$, and age in years). An effective amount of a pharmaceutical composition is that which provides an objectively identifiable improvement as noted by the clinician or other qualified observer. For example, alleviating a symptom of a disorder, disease or condition. As used herein, the term "dosage effective manner" refers to amount of a pharmaceutical composition to produce the desired biological effect in a subject or cell.

For example, the dosage unit form can comprise 1 nanogram to 2 milligrams, or 0.1 milligrams to 2 grams; or from 10 milligrams to 1 gram, or from 50 milligrams to 500 milligrams or from 1 microgram to 20 milligrams; or from 1 microgram to 10 milligrams; or from 0.1 milligrams to 2 milligrams.

In one embodiment, the unit dosage form comprises 25, 50, 75, 100, 200, or 300 milligrams of the active pharmaceutical ingredient, e.g., apilimod free base or apilimod dimesylate. In one embodiment, the unit dosage form is the form of a tablet or capsule for oral delivery.

The pharmaceutical compositions can take any suitable form (e.g, liquids, aerosols, solutions, inhalants, mists, sprays; or solids, powders, ointments, pastes, creams, lotions, gels, patches and the like) for administration by any desired route (e.g, pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). For example, a pharmaceutical composition of the invention may be in the form of an aqueous solution or powder for aerosol administration by inhalation or insufflation (either through the mouth or the nose), in the form of a tablet or capsule for oral administration; in the form of a sterile aqueous solution or dispersion suitable for administration by either direct injection or by addition to sterile infusion fluids for intravenous infusion; or in the form of a lotion, cream, foam, patch, suspension, solution, or suppository for transdermal or transmucosal administration.

A pharmaceutical composition can be in the form of an orally acceptable dosage form including, but not limited to, capsules, tablets, buccal forms, troches, lozenges, and oral liquids in the form of emulsions, aqueous suspensions, dispersions or solutions. Capsules may contain mixtures of a compound of the present invention with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. In the case of tablets for oral use, carriers which are commonly used include lactose and corn starch. Lubricating agents, such as magnesium stearate, can also be added. For oral administration in a capsule form, useful diluents include lactose and dried corn starch. When aqueous suspensions and/or emulsions are administered orally, the compound of the present invention may be suspended or dissolved in an oily phase is combined with emulsifying and/or suspending agents. If desired, certain sweetening and/or flavoring and/or coloring agents may be added.

A pharmaceutical composition can be in the form of a tablet. The tablet can comprise a unit dosage of a compound of the present invention together with an inert diluent or carrier such as a sugar or sugar alcohol, for example lactose, sucrose, sorbitol or mannitol. The tablet can further comprise a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. The tablet can further comprise binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures.

The tablet can be a coated tablet. The coating can be a protective film coating (e.g. a wax or varnish) or a coating designed to control the release of the active agent, for example a delayed release (release of the active after a predetermined lag time following ingestion) or release at a particular location in the gastrointestinal tract. The latter can be achieved, for example, using enteric film coatings such as those sold under the brand name Eudragit®.

Tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine.

A pharmaceutical composition can be in the form of a hard or soft gelatin capsule. In accordance with this formulation, the compound of the present invention may be in a solid, semi-solid, or liquid form.

A pharmaceutical composition can be in the form of a sterile aqueous solution or dispersion suitable for parenteral administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

A pharmaceutical composition can be in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions of the compound of the present invention as a free base or pharmacologically acceptable salt can be prepared in water suitably mixed with a surfactant. Examples of suitable surfactants are given below. Dispersions can also be prepared, for example, in glycerol, liquid polyethylene glycols and mixtures of the same in oils.

The pharmaceutical compositions for use in the methods of the present invention can further comprise one or more additives in addition to any carrier or diluent (such as lactose or mannitol) that is present in the formulation. The one or more additives can comprise or consist of one or more surfactants. Surfactants typically have one or more long aliphatic chains such as fatty acids which enables them to insert directly into the lipid structures of cells to enhance drug penetration and absorption. An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Thus, hydrophilic surfactants are generally considered to be those compounds having an HLB value greater than about 10, and hydrophobic surfactants are generally those having an HLB value less than about 10. However, these HLB values are merely a guide since for many surfactants, the HLB values can differ by as much as about 8 HLB units, depending upon the empirical method chosen to determine the HLB value.

Among the surfactants for use in the compositions of the invention are polyethylene glycol (PEG)-fatty acids and PEG-fatty acid mono and diesters, PEG glycerol esters, alcohol-oil transesterification products, polyglyceryl fatty acids, propylene glycol fatty acid esters, sterol and sterol derivatives, polyethylene glycol sorbitan fatty acid esters, polyethylene glycol alkyl ethers, sugar and its derivatives, polyethylene glycol alkyl phenols, polyoxyethylene-polyoxypropylene (POE-POP) block copolymers, sorbitan fatty acid esters, ionic surfactants, fat-soluble vitamins and their salts, water-soluble vitamins and their amphiphilic derivatives, amino acids and their salts, and organic acids and their esters and anhydrides.

The present invention also provides packaging and kits comprising pharmaceutical compositions for use in the methods of the present invention. The kit can comprise one or more containers selected from the group consisting of a bottle, a vial, an ampoule, a blister pack, and a syringe. The kit can further include one or more of instructions for use in treating and/or preventing a disease, condition or disorder of the present invention, one or more syringes, one or more applicators, or a sterile solution suitable for reconstituting a pharmaceutical composition of the present invention.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

EXAMPLES

Example 1

Apilimod is a Highly Selective Cytotoxic Agent in Cancer Cells

Figure 1B:
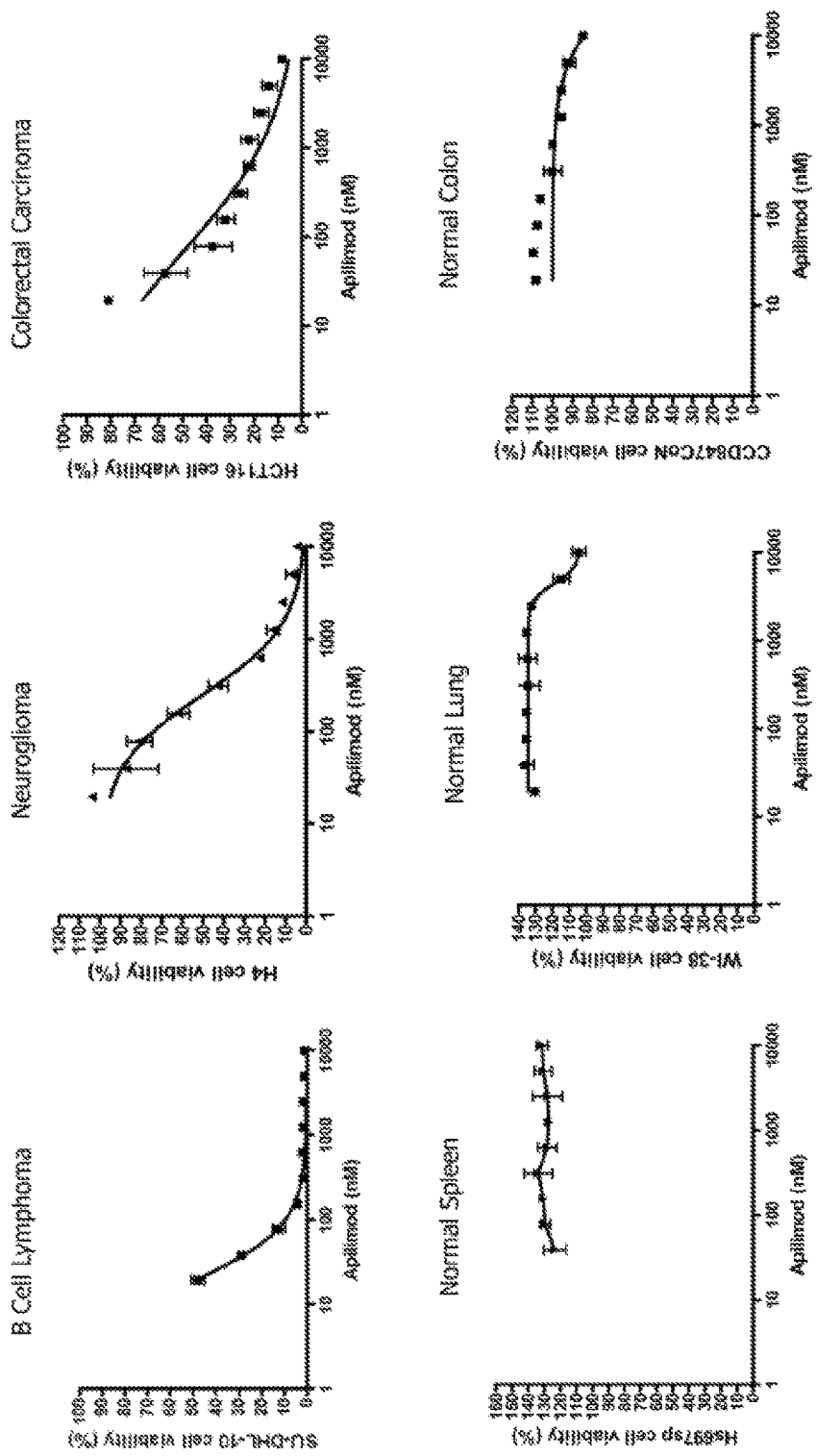
FIG. 1B: Effect of apilimod on cell viability in cancer cells compared to non-cancer (normal) cells.

Apilimod was identified in a high throughput cell viability screen using TSC2−/− mouse embryonic fibroblasts (TSC2−/− MEF) cells which are characterized by constitutively elevated mTOR signaling activity. Briefly, test compounds (5 μl stock solution, 6×desired final well concentration) were dispensed to 384-well assay plates, TSC2−/− MEF cells (1000 cells per well in 25 μL of media) were added to the plates and the plates were incubated for 72 h (3 days) at 37° C. under an atmosphere of 5% $CO_2$ in a humidified incubator for 3 days. Cell viability was determined with CellTiter-Glo® luminescence assay (Promega) per the manufacturer's instructions. Viability was expressed as a percentage of untreated control cells. As an example, for apilimod, MEF-EV cell viability (Mean+/−StDev, n=3) was 2.16+/−0.36% @ 0.5 μM and 1.94+/−0.07% @ 5 μM. In a 10 point dose-response curve, apilimod inhibited cell viability with an $IC_{50}$ of 19.5 nM for the TSC2−/− MEF cells tested (FIG. 1). We next tested apilimod on other cancer cell lines including a B-cell lymphoma (SUDHL-10), a neuroglioma (H4), and a colorectal carcinoma (HCT116) as well as on non-cancer (normal) cell lines derived from spleen, lung, and colon. In these cell viability assays, apilimod was a highly selective inhibitor of cell viability in the cancer cells versus the non-cancer (normal) cells as demonstrated by their much higher $IC_{50}$ values which ranged from 20-200 fold higher than those of the cancer cells. These results are shown in FIG. 1B.

The cytotoxic activity of apilimod was further evaluated in the 3-day CellTiterGlo™ assay using 122 human cancer cell lines representing 24 tumor types. In this 3-day assay, a cell line was called as apilimod sensitive if the $IC_{50}$ was less than 500 nM. 35 cell lines were identified as sensitive to apilimod-induced cytotoxicity in this assay. The apilimod-sensitive cells included cells derived from several different cancers including non-Hodgkin's lymphoma, Hodgkin's lymphoma, colorectal cancer, and lung cancer. The most sensitive of those tested were non-Hodgkin's Lymphoma (NHL) cell lines. Just over 50% of the NHL cell lines tested were sensitive to apilimod and certain subtypes of NHL were extremely sensitive to apilimod, with $IC_{50}$ values of less than 100 nM (compared to the cutoff for sensitive/insensitive in the screen, which was 500 nM). These included a human Burkitt's lymphoma (ST486), a human mantle cell lymphoma (JeKo-1) and a human DLBCL (SUDHL-4, $IC_{50}$=50 nM). The only NHL subtype not sensitive in this assay was follicular. Both DLBCL-GCB and -ABC subtypes were apilimod sensitive, indicating that apilimod may be effective against many NHL cancers, including the more aggressive subtypes that are often refractory to standard treatments.

NHL represents a diverse group of hematopoietic malignancies that vary in severity, with subtypes ranging from slow growing to aggressive. Subtypes of NHL include diffuse large B cell lymphoma (DLBCL), Burkitt's lymphoma, mantle lymphoma, and follicular B cell lymphoma. DLBCL is divided into two subtypes, GCB and ABC, based on gene expression and cell of origin. The GCB are germinal center B cell type, arising from normal germinal center B cells, and the ABC are activated B cell type, arising from post-germinal center B cells in the process of differentiating into plasma cells.

Figure 2A:
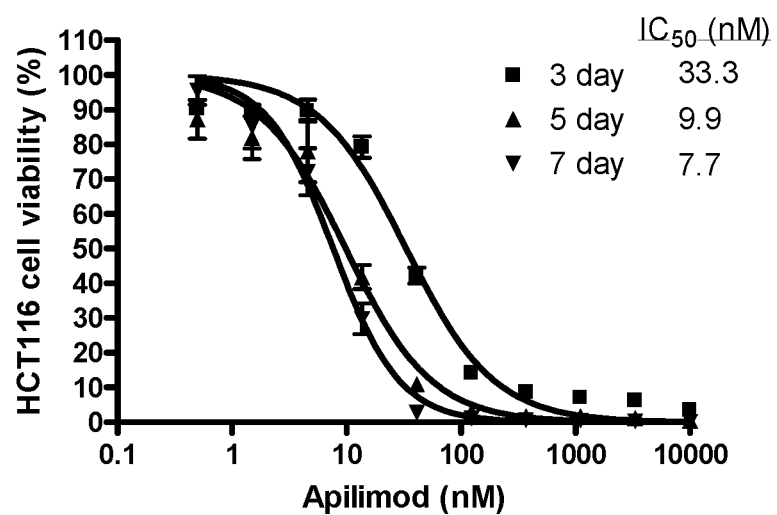
FIG. 2A: Ten point dose response of HCT116 colorectal carcinoma cells to apilimod at 3, 5, and 7 days incubation with compound.
Figure 2B:
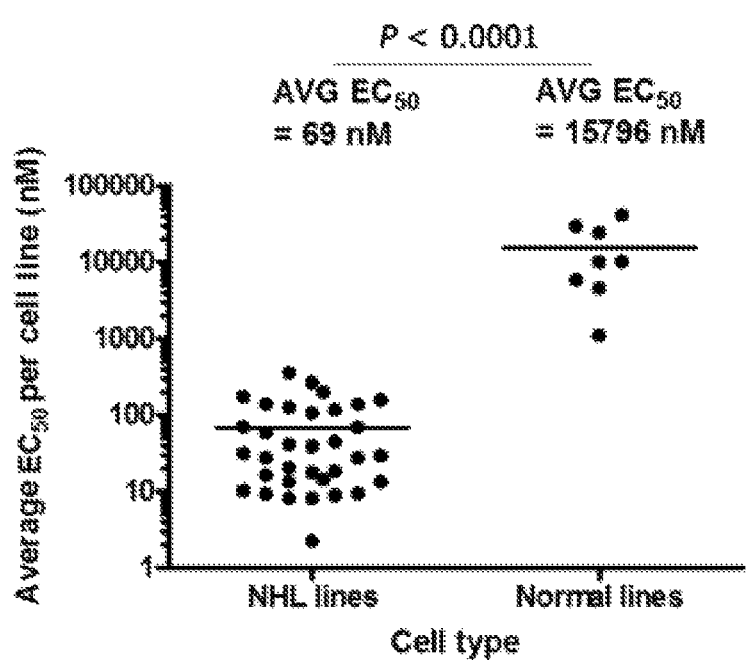
FIG. 2B: Sensitivity of different NHL subtypes to apilimod in a 7 day assay ($IC_{50}$ <125 nM).

We next tested apilimod in longer cell viability assays and compared the sensitivity of cells tested over 3, 5, and 7 days. The sensitivity of all cell lines increased with increasing time of exposure to apilimod, to an $IC_{50}$ of less than 125 nM for a 7-day exposure. This is exemplified in FIG. 2A for the HCT116 colorectal carcinoma cells. The different NHL subtypes also each showed increased sensitivity to apilimod ($IC_{50}$<125 nM) in the 7 day assay (FIG. 2B). And all NHL subtypes were sensitive in this assay, including mantle, follicular, Burkitt's, DLBCL-ABC, DLBCL-GCB, and double-hit DLBCL. Notably, all of the cell lines representing aggressive lymphomas were sensitive, including those having the double myc/bcl2 translocation ("double-hit DLBCL") as well as mantle cell lymphomas. Overall, 72% of the 32 NHL cell lines tested were sensitive to apilimod, with average $IC_{50}$ values of 69 nM, compared to 15.8 micromolar (uM) for non-cancer (normal) cells.

Example 2

Apilimod Synergizes with Components of CHOP

As discussed above, NHL cells demonstrated particular sensitivity to apilimod in our cancer cell line screens. DLBCL is the most common type of NHL, accounting for 30-40% of lymphomas in Western countries. DLBCL is an aggressive neoplasm of mature B cells. Approximately 40% of all DLBCL patients relapse after first line treatment. Many refractory DLBCL-GCB cancers exhibit single and double translocations of MYC and BCL2. Patients with these genetic variants tend to have a poorer prognosis due at least in part to overexpression of MYC and BCL2. Notably, apilimod was effective even in DLBCL-GCB cell lines exhibiting these translocations (Table 2), supporting a role for apilimod in the treatment of even aggressive subtypes of NHL, either alone, as monotherapy, or in combination with standard treatments.

TABLE 2

Bcl-2 and c-myc translocation status for B Cell Lymphoma Lines and their sensitivity to apilimod.

| Number | B Cell Lymphoma Model | Cell Line | $IC_{50}$ (nM) | Bcl-2 | C-myc |
|---|---|---|---|---|---|
| 7 | Human DLBCL-GCB | SUDHL-4 | 25 | Yes | Yes |
| 8 | Human DLBCL-GCB | SUDHL-6 | 80 | Yes | No |
| 9 | Human DLBCL-GCB | DB | 150 | No | No |
| 10 | Human DLBCL-GCB | Toledo | 270 | ND | ND |
| 11 | Human DLBCL-GCB | SUDHL-10 | 20 | Yes | Yes |
| 12 | Human DLBCL-GCB | WSU-DLCL2 | 160 | Yes | No |
| 13 | Human DLBCL-GCB | OCI-Ly19 | 380 | Yes | No |
| 20 | Human DLBCL-GCB | HT | 642 | ND | ND |
| 21 | Human DLBCL-GCB | Pfeiffer | 2,620 | ND | ND |

ND = No Data

When tested in vitro against other clinical agents active against NHL, apilimod proved to be one of the most potent drugs tested (Table 3).

TABLE 3

Comparison of IC50 values of apilimod and various chemotherapy drugs in a three-day assay.

| Drug | Cellular Target | $IC_{50}$ (nM) SU-DHL-4 | $IC_{50}$ (nM) WSU-DLCL2 |
|---|---|---|---|
| apilimod | PIKfyve | 23 | 54 |
| ibrutinib | BTK | 718 | 747 |
| idelalisib | PI3Kd | 2,034 | 6,154 |
| EPZ-6438 | EZH2 | >20,000 | >10,000 |
| ABT-199 | BCL-2 | 212 | 3,371 |
| duvelisib | PI3Kγ/δ | 13 | 863 |
| KPT-330 | XPO1 | 93 | 165 |

To further evaluate the effectiveness of apilimod against aggressive NHL tumors, the ability of apilimod to act synergistically with any of a number of chemotherapeutic agents that comprise the standard first line treatment for many such cancers was tested. These included, for example, cyclophosphamide, doxorubicin, vincristine and prednisone (referred to as the "CHOP" chemotherapy regimen), as well as the chemotherapeutic agent velcade, which is indicated for relapsed mantle cell lymphoma.

For synergy studies the following DLBCL-GCB cell lines were used: WSU-DLCL2, SUDHL-4 and SUDHL-6. Cells were seeded in 96 well plates at their optimum density. Cells were treated with either each agent alone or in combination with apilimod. Cells were treated for 72 h (3 days) before proliferation was assessed using CellTiterGlo® (Promega). For calculation of synergy, CalcuSyn (version 2.11, Biosoft) was used to determine the combination index (CI) as defined by Chou et al., *Adv. Enzyme. Regul.* (1984) 22:27-55. Thus, drug combinations producing CI values >1 were defined as antagonistic, CI=1 as additive, and CI<1 as synergistic.

As shown in Table 4, apilimod demonstrated synergistic activity with all agents tested (cyclophosphamide, doxorubicin, prednisolone, vincristine, and velcade) in all three cell lines. These results demonstrate that combination therapy with apilimod represents a promising new approach for addressing the unmet medical need for treatments that benefit patients who relapse after or who are refractory to standard chemotherapy regimens.

TABLE 4

| Combination Treatment | | WSU-DLCL2 | SU-DHL-4 | SU-DHL-6 |
|---|---|---|---|---|
| Standard of care | Cyclophosphamide (Mafosfamide) + Apilimod | Synergistic Apili 62.5 nM/Maf 625 nM Fa = 0.82; CI = 0.7 | Synergistic Apili 125 nM/Maf 1250 nM Fa = 0.82; CI = 0.7 | Synergistic Apili 125 nM/Maf 1250 nM Fa = 0..77; CI = 0.5 |
| | Doxorubicin + Apilimod | Synergistic Apili 62.5 nM/Dox 25 nM Fa = 0.99; CI = 0.4 | Synergistic Apili 500 nM/Dox 200 nM Fa = 0.88; CI = 0.9 | Synergistic Apili 250 nM/Dox 100 nM Fa = 0.86; CI = 0.1 |
| | Prednisolone + Apilimod | Synergistic Apili 15.6 nM/Pred 156 nM Fa = 0.97; CI = 0.3 | Synergistic Apili 125 nM/Pred 625 nM Fa = 0.85; CI = 0.5 | Synergistic Apili 250 nM/Pred 556 nM Fa = 0.85; CI = 0.2 |
| | Vincristine + Apilimod | Synergistic Apili 31.3 nM/Vin 0.3 nM Fa = 0.97; CI = 0.2 | Synergistic Apili 37 nM/Vin 1.25 nM Fa = 0.85; CI = 0.4 | Synergistic Apili 37 nM/Vin 1.25 nM Fa = 0.85; CI = 0.4 |
| Other therapies | Velcade + Apilimod | Synergistic Apili 250 nM/Vel 5 nM Fa = 0.99; CI = 0.3 | Synergistic Apili 37 nM/Vel 2.5 nM Fa = 0.98; CI = 0.2 | Synergistic Vel 2.5 Maf 625 nM Fa = 0.98; CI = 0.3 |

Summary of drug combination effects of apilimod and individual components of CHOP, Velcade or Everolimus in DLBCL-GCB cell lines. The concentration of apilimod (Apili) in combination with either CHOP (cyclophosphamide (mafosfamide, 20) = Maf; doxorabicin = Dox; vincristine = Vin; Prednisolone = Pred) components, or Velcade (Vel) to produce the Fraction effect (Fa) is shown. Combination index (CI) was used to determine combination effects, where CI > 1 is antagonistic, CI = 1 is additive and CI < 1 is synergistic, where the Fa > 0.75.

Example 3

Synergistic Activity Between Apilimod and Ibrutinib

Figure 3:
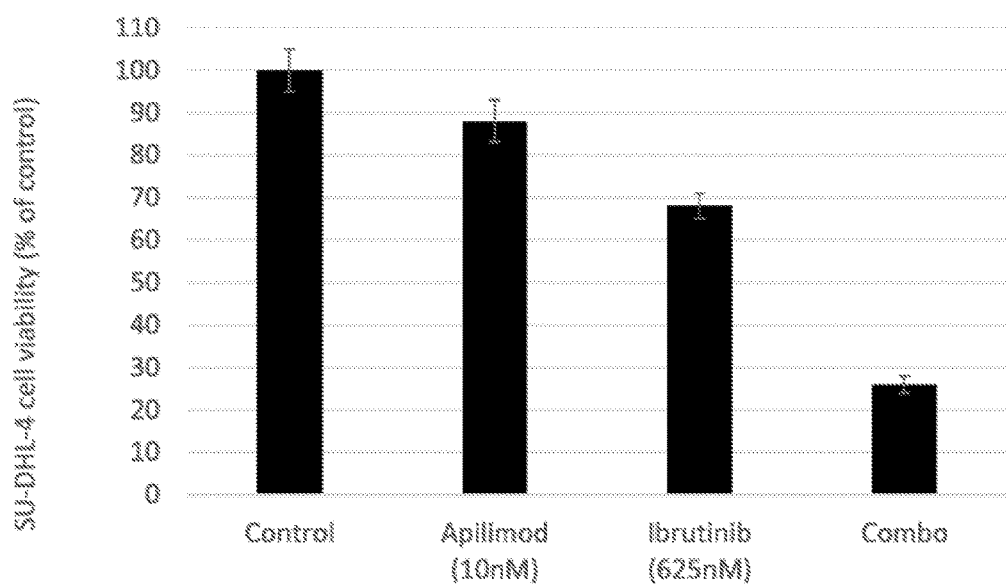
FIG. 3: Screening SU-DHL-4 cells with a manually curated library of 93 drugs with and without apilimod (10 nM) identified ibrutinib as a drug that when combined with apilimod exerts synergistic activity.

Ibrutinib is an FDA-approved drug targeting B-cell malignancies and indicated for monotherapy in treating mantle cell lymphoma and chronic lymphocytic leukemia. It is also known as PCI-32765 and marketed under the trade name Imbruvica™. Ibrutinib is a selective and covalent inhibitor of the enzyme Bruton's tyrosine kinase (BTK). BTK is a key mediator of at least three critical B-cell pro-survival mechanisms occurring in parallel-regulation of apoptosis, cell adhesion and cell migration and homing. The synergistic activity of apilimod with ibrutinib further indicate that apilimod is a promising agent for use in combination therapy with other chemotherapy agents, especially those targeted against B-cell lymphomas. Ibrutinib significantly reduced SUDHL-4 cell viability in the presence of apilimod compared with either ibrutinib or apilimod alone. See FIG. 3. This result was validated in two other cell lines tested—WSU-DLCL2 and SUDHL-6.

Example 4

Anti-Tumor Activity of Apilimod on DLBCL Tumors In Vivo

The ability of apilimod to inhibit tumor growth in vivo, both alone and in combination with ibrutinib was tested next. As described below, apilimod alone significantly reduced tumor growth and the combination of apilimod and ibrutinib provided greater growth inhibition than either agent alone.

The study objective was to evaluate pre-clinically the in vivo therapeutic efficacy of apilimod in the treatment of a subcutaneous SUDHL-6 human DLBCL cancer xenograft model alone, and in combination with ibrutinib.

In the first arm of the study, apilimod was tested alone. The SUDHL-6 cell line was maintained in RPMI-1640 medium supplemented with 10% fetal bovine serum and L-glutamine (2 mM) at 37° C. in an atmosphere of 5% $CO_2$. The tumor cells were sub-cultured twice weekly and harvested during exponential growth for tumor inoculation. NOD-SCID mice were γ-irradiated 24 hrs before inoculation. Each mouse was inoculated subcutaneously in the right flank with SU-DHL-6 tumor cells ($5\times10^6$) in 0.1 ml of PBS with Matrigel (1:1). The tumors were then grown to a mean size of approximately 80-120 mm$^3$ and the mice were then split into 5 groups and treated as detailed in the Table 5.

TABLE 5

Xenograft Model of DLBCL tumors

| Group | Treatment | Dose | Dosing schedule | Administration route | Number of mice |
|---|---|---|---|---|---|
| 1 | Vehicle (Saline) | — | QD × 5 -2 days off- QD × 5 | i.v. | 6 |
| 2 | Apilimod Dimesylate | 67.5 mg/kg (47 mg/kg Free Base) | QD × 5 -2 days off- QD × 5 | i.v. | 6 |
| 3 | 0.5% Methyl-cellulose | — | BID × 5 -2 days off- BID × 5 | p.o. | 6 |
| 4 | Apilimod Free Base | 75 mg/kg | BID × 5 -2 days off- BID × 5 | p.o. | 6 |
| 5 | Apilimod Free Base | 150 mg/kg | QD × 5 -2 days off- BID × 5 | p.o. | 6 |

Figure 4:
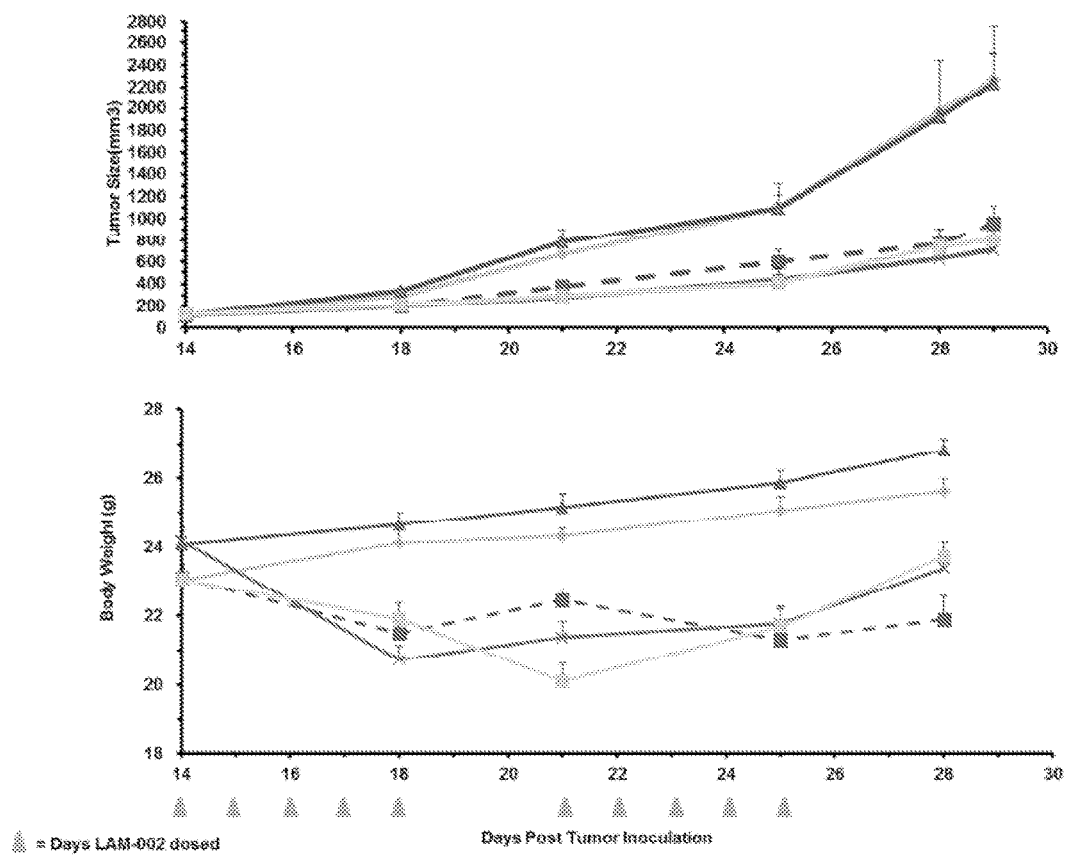
FIG. 4: Apilimod inhibits the growth of SU-DHL-6 DLBCL xenograft tumors; Top line shows vehicle saline (diamond, light grey solid lines) QD ×5, 2 days off, QD ×5 i.v.; 0.5% methylcellulose (triangle, solid dark grey lines) QD ×5, 2 days off, QD ×5 p.o.; apilimod dimesylate (square, dashed lines) 67.5 mg/kg (47 mg/kg free base) QD ×5 i.v., 2 days off, QD ×5; apilimod free base (square, light grey solid lines) 150 mg/kg QD ×5, 2 days off, QD ×5 p.o; apilimod free base (cross, solid lines) 75 mg/kg BID ×5, 2 days off, BID ×5 p.o.

Tumor size was measured twice a week in two dimensions using a caliper, and the volume is expressed in mm$^3$ using the formula: $V=0.5\ a\times b^2$ where a and b are the long and short diameters of the tumor, respectively. The mice were monitored for 29 days and significant growth inhibition was observed in all apilimod treatment arms. Intravenous administration reduced tumor size by 58% (47 mg/kg) and oral dosing reduced growth by 68% (150 mg/kg split dose) or by 64% (150 mg/kg single dose) with negligible effect on body weight (see FIG. 4). Thus, intravenous and oral administrations of apilimod displayed similar efficacy in impairing the growth of SU-DHL-6 tumors in vivo.

The second arm of the study evaluated efficacy of apilimod when combined with ibrutinib in the same SUDHL-6 human DLBCL cancer xenograft model using the same protocol as described above. Each mouse was inoculated subcutaneously in the right flank with SU-DHL-6 tumor cells ($5\times10^6$) in 0.1 ml of PBS with Matrigel (1:1). The tumors were then grown to a mean size of approximately 80-120 mm$^3$ and the mice were then split into 6 groups and treated as detailed in the Table 6.

TABLE 6

SUDHL-6 cell line xenograft experiment

| Group | Treatment | Dose | Dosing schedule | Administration route | Number of mice |
|---|---|---|---|---|---|
| 1 | Vehicle | NA | QD × 5-2 days off- QD × 5 | p.o. + i.v. | 6 |
| 2 | Apilimod Free Base | 75 mg/kg | QD × 5-2 days off- QD × 5 | p.o. | 6 |
| 3 | Ibrutinib | 10 mg/kg | QD × 12 | i.v. | 6 |
| 4 | Ibrutinib | 20 mg/kg | QD × 12 | i.v. | 6 |
| 5 | Apilimod Free Base + Ibrutinib | 75 mg/kg + 10 mg/kg | QD × 5-2 days off- QD × 5 + QD × 12 | p.o. + i.v. | 6 |
| 6 | Apilimod Free Base + Ibrutinib | 75 mg/kg + 20 mg/kg | QD × 5-2 days off- QD × 5 + QD × 12 | p.o. + i.v. | 6 |

Tumor size was measured twice a week in two dimensions using a caliper, and the volume is expressed in mm$^3$ using the formula: V=0.5 a×b$^2$ where a and b are the long and short diameters of the tumor, respectively. The mice were monitored for 31 days and significant growth inhibition was observed in the 75 mg/kg apilimod (57%), 10 mg/kg ibrutinib (54%), and 20 mg/kg ibrutinib (64%) treatment arms. The combination of 75 mg/kg apilimod with ibrutinib further reduced tumor growth in a dose dependent manner; 10 mg/kg ibrutinib (65%) and 20 mg/kg ibrutinib (70%) (see FIG. 5.

Example 5

Apilimod is a Highly Selective Binder of PIKfyve Kinase

In order to identify the cellular target of apilimod in cancer cells, whole cell lysate prepared from human neuroglioma cells was used to identify its binding partners using chemical capture mass spectrometry (CCMS). This work was performed at Caprotec Bioanalytics GmbH, Berlin Germany. See Michaelis et al., *J. Med. Chem.*, 55 3934-44 (2012) and references cited therein. Briefly, two capture compound variants employing apilimod as selectivity function attached in a single orientation were synthesized and analyzed by LC-MS and 1H-NMR to ensure identity and purity. Capture conditions were optimized in whole cell lysate, e.g. minimization of non-specific interactions of the proteins with capture compounds, concentration of reagents and proteins to obtain maximum binding of proteins and capture compounds, etc. One capture compound was selected to identify specific protein binders in the CCMS experiments using apilimod as a competitor ligand. Proteins that are detected by LC-S in the capture assay and that are significantly diminished in competition control experiments are considered to be specific binders. These specific binders were further subjected to stringent data analysis criteria to determine specificity after unbiased data evaluation. Specific protein binders were ranked according to their fold change (FC) values in the capture experiments. Only two proteins were identified as high probability candidate target proteins of apilimod: PIKfyve and Vac14. FC and p-values for these proteins in the four different capture compound concentration experiments are shown in Table 7.

TABLE 7

| | | Capture Compound Concentrations | | | |
|---|---|---|---|---|---|
| | | 0.1 µM | 0.5 µM | 1.0 µM | 2.0 µM |
| PIKfyve | log$_2$ (FC) | 6.3 | 6.2 | 4.1 | 4.3 |
| | −log$_{10}$ (p-value) | 3.7 | 2.8 | 5.1 | 3.9 |
| Vac14 | log$_2$ (FC) | 6.2 | 5.6 | Inf. | 3.9 |
| | −log$_{10}$ (p-value) | 3.9 | 3.8 | 1.9 | 3.6 |

Figure 6:
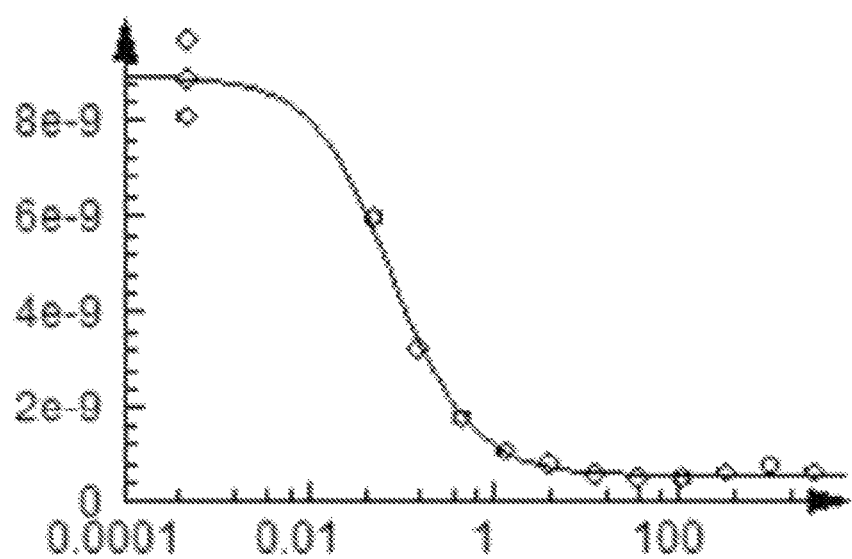
FIG. 6: Apilimod binds with high affinity to PIKfyve (Kd=75 pM).

In a separate study, protein kinase profiling of apilimod was conducted to identify kinase targets (DiscoveRx, Fremont, Calif.). A dissociation constant (K$_d$) study was performed using apilimod at increasing concentrations (0.05-3000 nM) against PIKfyve, a known target of apilimod. The experiment was performed in duplicate and the K$_d$ was determined to be 0.075 nM (range 0.069-0.081 nM) (FIG. 6).

Next, apilimod was screened against a comprehensive panel of kinases (PIKfyve not included). In total, 456 kinases, including disease-relevant kinases, were assayed for their ability to bind with apilimod. The screening concentration of apilimod was 1 µM, a concentration that is >10,000 times greater than the K$_d$ for apilimod against PIKfyve. The results from the screen showed that apilimod did not bind to any of the 456 kinases tested.

Together, these results demonstrate that apilimod binds with high selectivity in cancer cells to a single cellular kinase, PIKfyve. PIKfyve is an enzyme that binds to PI(3)P and catalyzes the formation of the lipid second messengers PI(3,5)P2 and PI(5)P and others have shown that apilimod is also a potent and specific inhibitor of this kinase PIKfyve in normal cells. Cai X et al., *Chem Biol.* 2013 Jul. 25; 20(7): 912-21. As discussed in more detail below, in order to understand the mechanism of apilimod's selective cytotoxicity against cancer cells, we conducted a series of experiments aimed at elucidating its biological activity in cancer cells.

Example 6

Mechanism of Anti-cancer Activity of Apilimod

Apilimod is known to be a potent inhibitor of the inflammatory cytokines IL-12 and IL-23. To the extent apilimod was indicated for treating a disease or disorder, it was predicated on this activity. Although the clinical testing of apilimod focused on its potential efficacy in autoimmune and inflammatory diseases such as psoriasis, rheumatoid arthritis, and Crohn's disease, there were a few published suggestions that apilimod might be useful against cancers, and specifically against cancers in which c-rel or IL-12/23 were acting as pro-proliferative factors. See e.g., WO 2006/128129 and Baird et al., *Frontiers in Oncology* 3:1 (2013), respectively. Surprisingly, and contrary to these expectations predicated on apilimod's IL-12/23 inhibitory activity, we found no correlation between any of c-Rel expression (c-Rel is a transcription factor for the IL-12/23 genes), IL-12, or IL-23 expression and sensitivity to apilimod in the tested cell lines. Briefly, gene expression data from the Cancer Cell Line Encyclopedia (CCLE) was analyzed for the 22 B cell lymphoma lines for which we obtained dose response curves against apilimod (see Table 8).

TABLE 8

22 B Cell Lymphoma Lines analyzed for gene expression and response to apilimod. Epstein Barr status and nuclear cREL status is noted.

| Number | B Cell Lymphoma Model | Cell Line | IC50 (nM) | EBV | Nuclear REL |
|---|---|---|---|---|---|
| 1 | Human Burkitt's lymphoma | ST486 | 25 | No | ND |
| 2 | Human Burkitt's lymphoma | Daudi | 200 | Yes | Yes |
| 3 | Human Burkitt's lymphoma | EB1 | 174 | Yes | ND |
| 4 | Human Burkitt's lymphoma | GA-10 | 382 | No | ND |
| 5 | Human Mantle Cell Lymphoma | Rec-1 | 300 | No | ND |
| 6 | Human Mantle Cell Lymphoma | JeKo-1 | 70 | No | ND |
| 7 | Human Diffuse Large B Cell Lymphoma -GCB | SUDHL-4 | 25 | No | Yes |
| 8 | Human Diffuse Large B Cell Lymphoma -GCB | SUDHL-6 | 80 | No | ND |
| 9 | Human Diffuse Large B Cell Lymphoma -GCB | DB | 150 | No | ND |
| 10 | Human Diffuse Large B Cell Lymphoma -GCB | Toledo | 270 | No | ND |
| 11 | Human Diffuse Large B Cell Lymphoma -GCB | SUDHL-10 | 20 | No | ND |
| 12 | Human Diffuse Large B Cell Lymphoma -GCB | WSU-DLCL2 | 160 | No | ND |
| 13 | Human Diffuse Large B Cell Lymphoma -GCB | OCI-Ly19 | 380 | Yes | ND |
| 14 | Human Burkitt's lymphoma | Namalwa | 600 | Yes | ND |
| 15 | Human Burkitt's lymphoma | CA46 | >10,000 | No | ND |
| 16 | Human Burkitt's lymphoma | Raji | >10,000 | Yes | Yes |
| 17 | Human Mantle Cell Lymphoma | GRANTA-519 | >10,000 | Yes | ND |
| 18 | Human Follicular B Cell Lymphoma | RL | >10,000 | ND | ND |
| 19 | Human Follicular Lymphoma - DLBCL-GCB | DOHH-2 | 700 | No | ND |
| 20 | Human Diffuse Large B Cell Lymphoma -GCB | HT | 642 | No | ND |
| 21 | Human Diffuse Large B Cell Lymphoma -GCB | Pfeiffer | 2,620 | ND | ND |
| 22 | Human Diffuse Large B Cell Lymphoma -GCB | KARPAS-422 | >10,000 | No | ND |

ND = No Data

Expression of c-REL was compared in sensitive ($IC_{50}$ less than 500 nM) and insensitive ($IC_{50}$ greater than 500 nM) lines by unpaired t-test. No statistically significant relationship between c-REL expression and sensitivity was found (p=0.97). Furthermore, no detection of a significant relationship between sensitivity to apilimod and either the presence of constitutive nuclear c-REL or infection with Epstein Barr virus in cell lines for which data has been published was found. The cell lines tested included the following apilimod sensitive (#1-13) and insensitive (#14-22) B cell lymphoma lines: Human Burkitt's lymphoma cell lines 1-4 (ST486, Daudi, EB1, GA-10), Human Mantle Cell Lymphoma 5-6 (Rec-1, JeKo-1), Human Diffuse Large B Cell Lymphoma-GCB 7-13 (SUDHL-4, SUDHL-6, DB, Toledo, SUDHL-10, WSU-DLCL2, OCl-Ly19), Human Burkitt's Lymphoma 14-16 (Namalwa, CA46, Raji), Human Mantle Cell Lymphoma 17 (GRANTA-519), Human Follicular B Cell Lymphoma 18 (RL), Human Follicular Lymphoma-DLBCL-GCB 19 (DOHH-2), Human Diffuse Large B Cell Lymphoma-GCB (HT, Pfeiffer, KARPAS-422).

The expression of IL-12A, IL-12RB1, IL-12RB2, IL-12B, IL-23A and IL-23R was further analyzed in a diverse group of 75 cancer cell lines, including the aforementioned 22 lymphoma lines (see Table 9).

TABLE 9

Various Cancer cell lines

| Number | Cancer Model | Cell Line | IC50 (nM) |
|---|---|---|---|
| 1 | Human Burkitt's lymphoma | ST486 | 25 |
| 2 | Human Mantle Cell Lymphoma | JeKo-1 | 70 |
| 3 | Human Diffuse Large B Cell Lymphoma -GCB | SUDHL-4 | 25 |
| 4 | Human Diffuse Large B Cell Lymphoma -GCB | SUDHL-6 | 80 |
| 5 | Human Burkitt's lymphoma | Daudi | 200 |
| 6 | Human histiocytic lymphoma | U937 | 106 |
| 7 | Human lung carcinoma | A549 | 110 |
| 8 | Human colorectal cancer | HCT116 | 125 |
| 9 | Human B-cell lymphoma | DB | 150 |
| 10 | Human Diffuse Large B Cell Lymphoma -GCB | WSU-DLCL2 | 160 |
| 11 | Human Colorectal | HCT-15 | 200 |
| 12 | Human Colorectal | SW480 | 90 |
| 13 | Human Colorectal | COLO-205 | 380 |
| 14 | Human Colorectal | SW620 | 90 |
| 15 | Human T-cell leukemia | Jurkat | 200 |
| 16 | Human neuroglioma | H4 | 250 |
| 17 | Human Diffuse Large B Cell Lymphoma -GCB | Toledo | 270 |
| 18 | Human B cell Non-Hodgkin's Lymphoma | Rec-1 | 300 |
| 19 | Human Hodgkin's lymphoma | KMH-2 | 181 |
| 20 | Human Burkitt's lymphoma | EB1 | 174 |
| 21 | Human Diffuse Large B Cell Lymphoma -GCB | SUDHL-10 | 20 |
| 22 | Human Burkitt's lymphoma | GA-10 | 382 |
| 23 | Human Diffuse Large B Cell Lymphoma -GCB | OCI-Ly19 | 380 |
| 24 | Human Diffuse Large B Cell Lymphoma -GCB | HT | 642 |
| 25 | Human Diffuse Large B Cell Lymphoma -GCB | Pfeiffer | 2,620 |
| 26 | Human Burkitt's lymphoma | Namalwa | 600 |
| 27 | Human Follicular B Cell Lymphoma-GCB | DOHH-2 | 700 |
| 28 | Human Bladder carcinoma (GATOR-/-) | SW780 | 1000 |
| 29 | Human colorectal cancer | MDST8 | 1000 |
| 30 | Human Burkitt's lymphoma | Raji | 10,000 |
| 31 | Human Hodgkin's lymphoma | HD-MyZ | >1000 |
| 32 | Human Hodgkin's lymphoma | L540 | >1000 |
| 33 | Human Hodgkin's lymphoma | HDLM-2 | >1000 |
| 34 | Human Burkitt's lymphoma | CA46 | >10,000 |
| 35 | Human Anaplastic Large Cell Lymphoma | SUDHL-1 | 590 |
| 36 | Human lung carcinoma | H1734 | 1500 |
| 37 | Human colorectal cancer | SW1116 | 1500 |
| 38 | Human Colorectal | COLO-320DM | 2,060 |
| 39 | Human neuroblastoma | A172 | 2000 |
| 40 | Human lung carcinoma | H1693 | 2000 |
| 41 | Human lung carcinoma | H460 | >2000 |
| 42 | Human lung carcinoma | H358 | >2000 |
| 43 | Human pancreatic cancer | CAPAN2 | >2000 |
| 44 | Human pancreatic cancer | PANC1 | >2000 |

TABLE 9-continued

Various Cancer cell lines

| Number | Cancer Model | Cell Line | IC50 (nM) |
|---|---|---|---|
| 45 | Human pancreatic cancer | MiaPaCa-2 | >2000 |
| 46 | Human pancreatic cancer | AsPC1 | >2000 |
| 47 | Human prostate cancer | DU145 | >2000 |
| 48 | Human acute myelogenous leukemia | KG-1 | >2500 |
| 49 | Human prostate cancer | LnCap | 3000 |
| 50 | Human T-cell lymphoma | HH | 3,300 |
| 51 | Human T-cell leukemia | MOLT-4 | 3,300 |
| 52 | Human prostate cancer | 22RV1 | >5000 |
| 53 | Human colorectal cancer | DLD-1 | >5000 |
| 54 | Human myelogenous leukemia | K562 | >5000 |
| 55 | Human colorectal cancer | RKO | >5000 |
| 56 | Human ovarian | TOV-21G | 7000 |
| 57 | Human prostate cancer | PC-3 | 10,000 |
| 58 | Human Hodgkin's lymphoma | L428 | 10,000 |
| 59 | Human plasmacytoma | RPMI-8226 | >10,000 |
| 60 | Human lung carcinoma | NCI-1975 | >10,000 |
| 61 | Human breast cancer | CAMA1 | >10,000 |
| 62 | Human neuroblastoma | SW1088 | >10,000 |
| 63 | Human neuroblastoma | M0591K | >10,000 |
| 64 | Human neuroblastoma | U-118 MG | >10,000 |
| 65 | Human neuroblastoma | U-87 MG | >10,000 |
| 66 | Human acute monocytic leukemia | THP1 | >10,000 |
| 67 | Human Diffuse Large B Cell Lymphoma -GCB | KARPAS-422 | >10,000 |
| 68 | Human Follicular B Cell Lymphoma | RL | >10,000 |
| 69 | Human Mantle Cell Lymphoma | GRANTA-519 | >10,000 |
| 70 | Human bronchioalveolar | NCI-H1650 | >20,000 |
| 71 | Human bronchioalveolar | SW1573 | >20,000 |
| 72 | Human bronchioalveolar | NCI-H1781 | >20,000 |
| 73 | Human bronchioalveolar | NCI-H1666 | 20,000 |
| 74 | Human Colorectal | LOVO | >10,000 |
| 75 | Human Colorectal | HT-29 | >10,000 |

Figure 7:
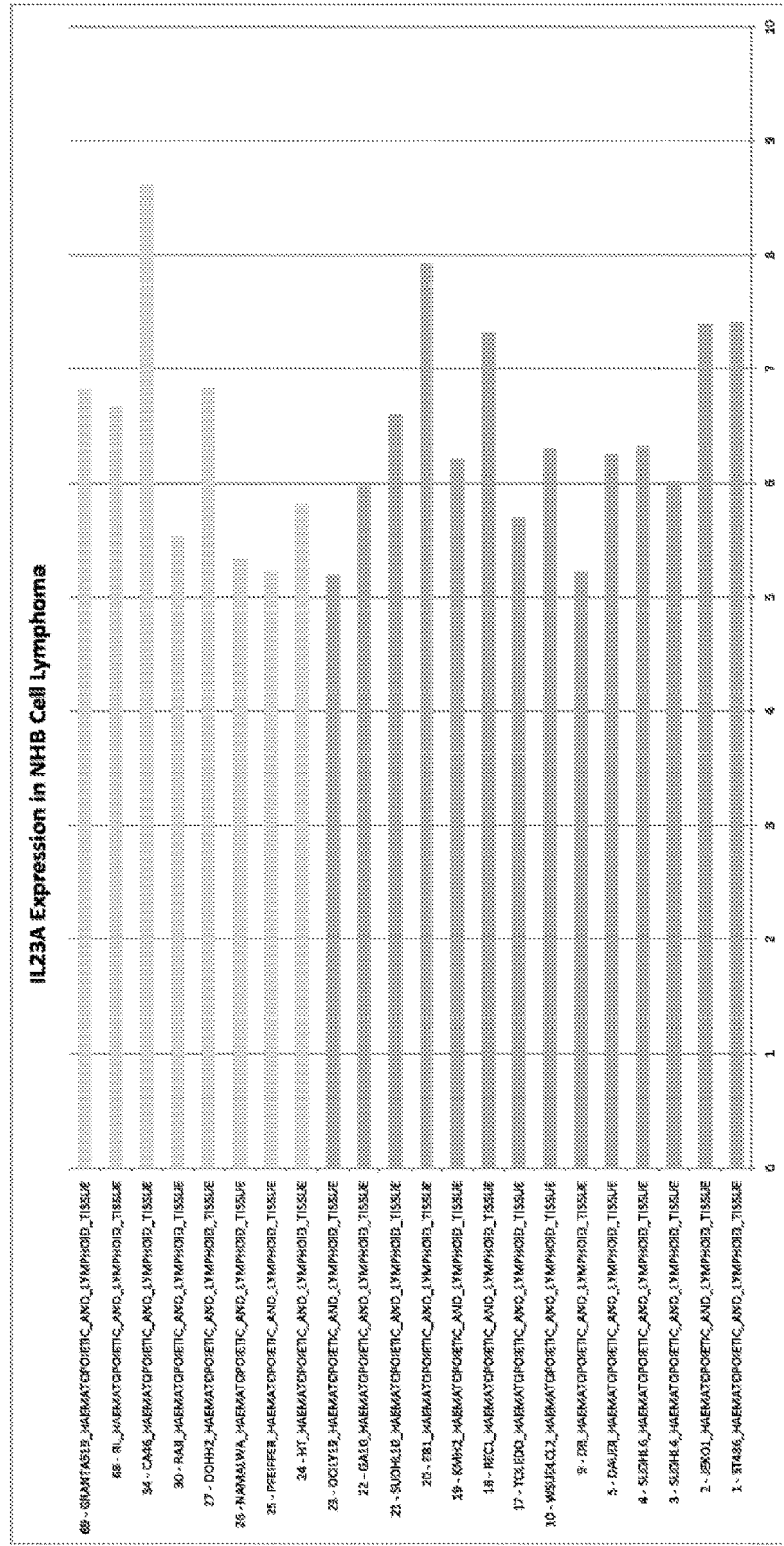
FIG. 7: IL-23A expression is not a statistically significant predictor of sensitivity in Non-Hodgkin's B cell lymphoma. Shown are apilimod sensitive NHB cell lines (bottom, dark) and insensitive (top, light).

Briefly, gene expression data from the CCLE was analyzed for the 75 cancer cell lines for which dose response curves against apilimod were obtained. The expression of each interleukin gene was compared in sensitive ($IC_{50}$ less than 500 nM) and insensitive ($IC_{50}$ greater than 500 nM) lines by unpaired t-test. No statistically significant relationship was found with the sole exception of IL-23A (p=0.022). IL-23A has been previously noted to be elevated in apilimod sensitive non-small cell lung cancer lines, and recombinant IL-23A was noted to increase proliferation of non-small cell lung cancer lines (see Baird et al. 2013, supra). Importantly, the statistical significance of IL-23A expression in sensitive cancer lines appears to be driven entirely by just two colon cancer lines. Furthermore IL-23A expression is not a statistically significant predictor of sensitivity in Non-Hodgkin's B cell lymphoma (FIG. 7).

Figure 8A:
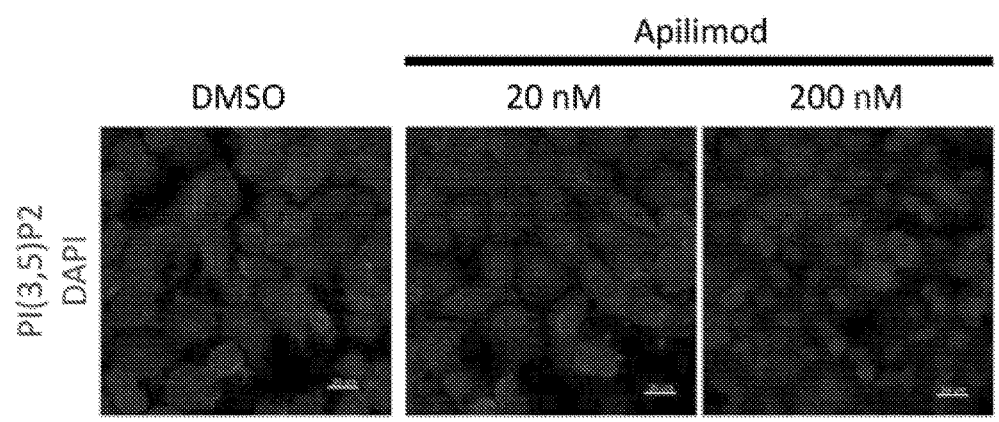
FIG. 8A: Immunostaining of the phosphoinositide PI(3,5)$P_2$ in H4 neuroglioma cells treated with the indicated concentration of apilimod for 24 hrs.
Figure 8B:
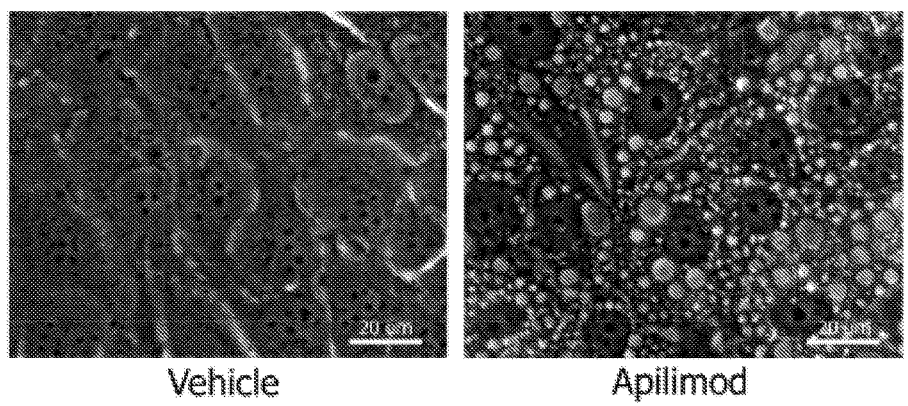
FIG. 8B: Differential Interference Contrast (DIC) images of H4 neuroglioma cells treated with either vehicle (left) or 100 nM apilimod (right) for 24 hrs.)

PIKfyve produces the lipid products $PI(3,5)P_2$ and PI5P, which in turn serve to establish membrane identity and control endolysosomal dynamics. Studies have shown that the $PI(3,5)P_2$ depletion arising from inhibition of PIKfyve produces a swollen endolysosome phenotype. Based on these studies, we tested the relationship between apilimod, PIKfyve inhibition and endolysosomal dysfunction. As shown in FIG. 8 our experiments demonstrated that apilimod induces approximately a 70% decrease of $PI(3,5)P_2$ in H4 neuroglioma cells after 24 h (FIG. 8A) and these cells exhibit a striking swollen endolysosomal (vacuole) phenotype (FIG. 8B). This phenotype was reversible, and cancer cell lines reverted to normal appearance within 3-4 days after drug removal.

Figure 9A:
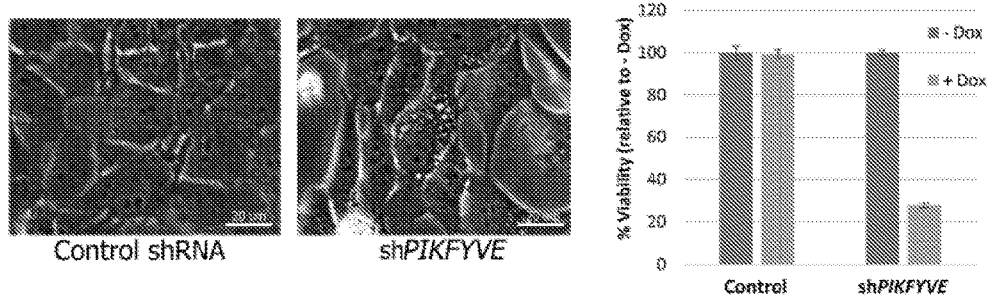
FIG. 9A: Left: DIC images of H4 transduced with either non-targeting shRNA (control) or hairpin targeted to PIK-FYVE (shPIKFYVE). Right: Viability of H4 cells after the induction of either control or PIKFYVE shRNA with doxycycline.
Figure 9B:
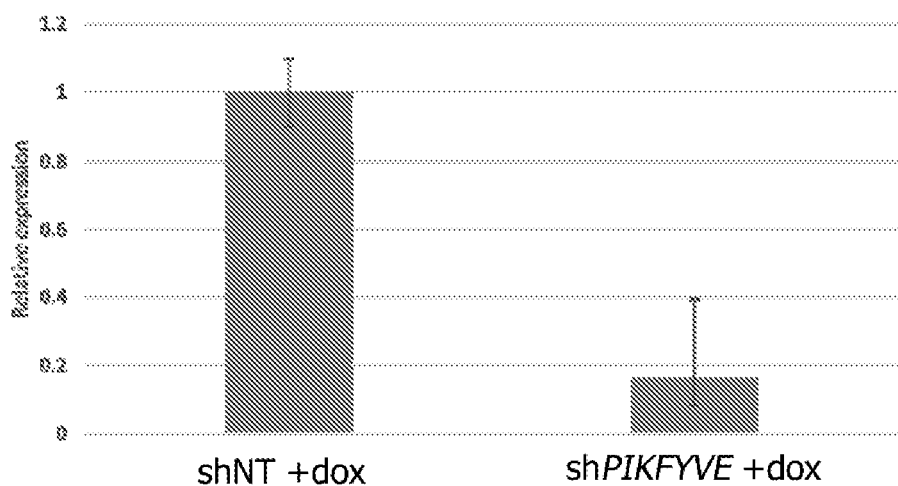
FIG. 9B: PIKFYVE knockdown in H4 neuroglioma.

We next tested whether repression of the PIKfyve gene product could recapitulate the cytotoxic effect seen with apilimod in one of the cell lines tested, the H4 neuroglioma cells. As shown in FIG. 9 the induction of a doxycycline-inducible hairpin targeting PIKFYVE transcript induced a swollen endolysosomal phenotype and a dramatic decrease in cell viability in H4 cells.

Together the data presented here support the conclusion that apilimod's anti-cancer properties arise through its inhibition of PIKfyve.

Example 7

Pharmacokinetics of Apilimod in Humans

Our preclinical data suggests that apilimod could be active in NHL patients if suitable plasma concentrations can be achieved in clinical trials. The pharmacokinetics (PK) of apilimod has been established in Phase 1 trials, although not previously reported. Briefly, the PK parameters of apilimod in normal healthy volunteers were determined after single day oral administration either as 1 dose or divided into 2 doses 10 hours apart according to the following dosing schema (Table 10).

TABLE 10

Phase 1, dose-escalation (QD/BID) study in normal healthy volunteers. Subjects were randomized to receive either active or placebo. Dosing was done on one day wth QD dosing in AM only and BID dosing in AM and PM.

| Cohort | Dose per admin | Frequency | Total Dose |
|---|---|---|---|
| A | 7 mg | once | 7 mg |
| B | 7 mg | ×2 | 14 mg |
| C | 14 mg | ×2 | 28 mg |
| D | 35 mg | ×2 | 70 mg |
| E | 70 mg | ×2 | 140 mg |
| F | 105 mg | ×2 | 210 mg |

Figure 5:
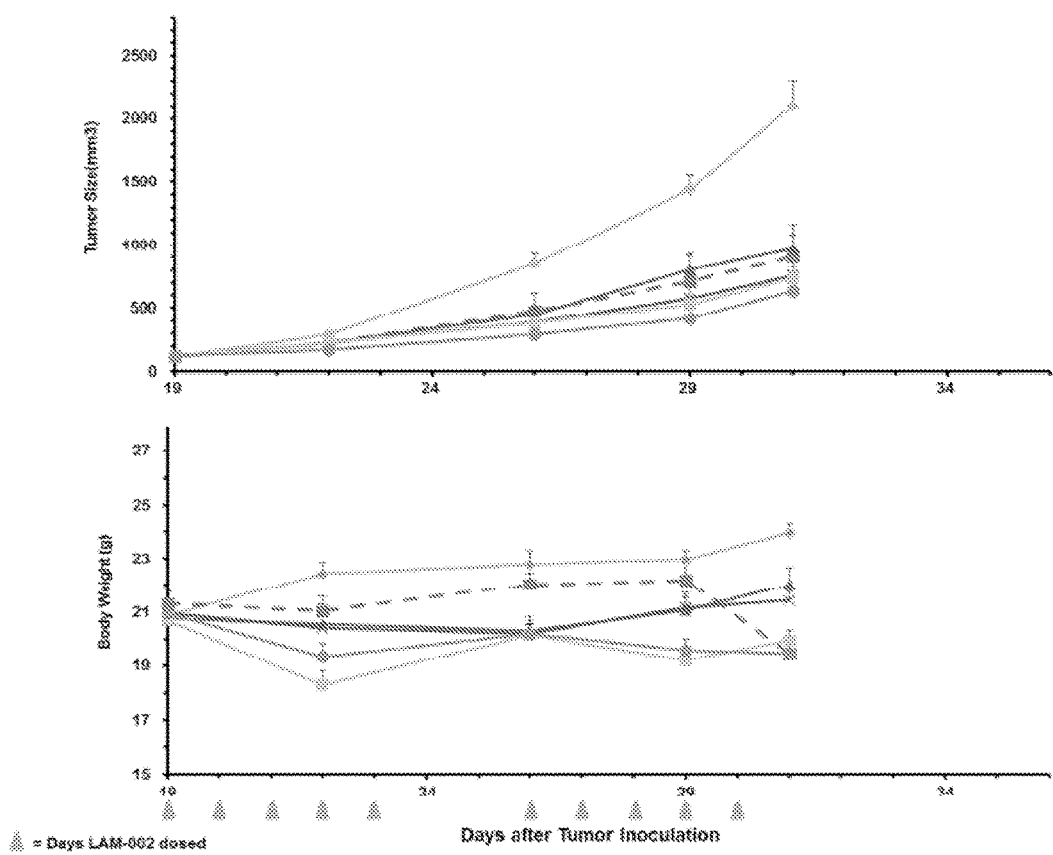
FIG. 5: Antitumor activity of apilimod in combination with ibrutinib on DLBCL tumors in vivo; Top line shows vehicle (diamond, light grey solid lines) QD ×5, 2 days off, QD ×5 p.o.+i.v.; ibrutinib (triangle, solid dark grey lines) 10 mg/kg QD ×12 i.v.; apilimod free base (square, dashed lines) 75 mg/kg QD ×5, 2 days off, QD ×5 p.o.; ibrutinib (cross, solid dark line) 20 mg/kg QD ×12 i.v.; apilimod free base 75 mg/kg QD ×5, 2 days off, QD ×5 p.o.+ibrutinib 10 mg/kg QD ×12 i.v. (square, solid light grey lines); apilimod free base 75 mg/kg QD ×5, 2 days off, QD ×5 p.o.+ibrutinib 10 mg/kg QD ×12 i.v. (circle, solid medium grey lines).

PK curves of apilimod concentrations over time are shown in FIG. 5. At 105 mg BID (210 mg total daily dose), apilimod had mean plasma concentrations of 192 and 149 ng/ml in the AM and PM, respectively (Table 11).

TABLE 11

Summary of combined male and female PK parameters for apilimod free base in human plasma.

| Treatment | Dose (mg)[a] | AM $C_{max}$ (ng/ml) | PM $C_{max}$ (ng/ml) |
|---|---|---|---|
| A | 7 | 10.8 +/− 2.7 | NA |
| B | 14 | 12.7 +/− 5.9 | 8.18 +/− 2.73 |
| C | 28 | 18.2 +/− 5.8 | 10.7 +/− 5.0 |
| D | 70 | 71.8 +/− 17.1 | 63.0 +/− 22.6 |
| E | 140 | 145 +/− 30 | 110 +/− 43 |
| F | 210 | 192 +/− 51 | 149 +/− 38 |

[a]Dose administered BID with 10 hr between AM and PM doses, except cohort A, which received a single dose. The number of subjects was n = 9 for all cohorts except E, where one subject was not included in the analysis due to anomalous concentrations. C max values shown are means for the 8 or 9 subjects.

Furthermore, for ~50% of the 24 hr period, apilimod plasma concentrations remained above 50 ng/ml (equal to 125 nM); the cut-off $IC_{50}$ for sensitivity in FIG. 3B. These plasma concentrations would also be expected to have a pharmacodynamic (PD) effect because apilimod induces vacuole formation in peripheral blood mononuclear cells after treatment for 24 h.

Apilimod had a tolerable safety profile at 105 mg BID, although the majority of the previous sponsor's Phase 2 efficacy studies in chronic inflammatory disease conditions were performed at total daily doses of 100 mg (or lower). These data demonstrate that concentrations of apilimod capable of potently suppressing NHL growth in vitro and likely to have a PD effect are achievable in humans, thus supporting our planned Phase 1 dose escalation study of apilimod in NHL.

What is claimed is:

1. A pharmaceutical composition for treating cancer in a subject, the composition comprising apilimod, or a pharmaceutically acceptable salt thereof, and an inhibitor of a checkpoint signaling pathway involving a programmed death 1 (PD-1) receptor and/or its ligands (PD-L1/2).

2. The composition of claim 1, wherein the inhibitor is selected from BMS-936559/MDX-1105, MPDL3280A (atezolizumab), MSB0010718C (avelumab), MED14736 (durvalumab), CT-011/pidilizumab, BMS-936558/MDX-1106/nivolumab, and pembrolizumab, and combinations of two or more of any of the foregoing.

3. The composition of claim 1, wherein the composition further comprises one or more of ondansetron, granisetron, dolasetron, palonosetron, pindolol and risperidone.

4. The composition of claim 1, wherein the composition comprises apilimod dimesylate and MPDL3280A (atezolizumab).

* * * * *